(12) United States Patent
Lee

(10) Patent No.: US 9,695,916 B2
(45) Date of Patent: Jul. 4, 2017

(54) DIFFERENTIAL MEMBER

(71) Applicant: LIVSMED INC., Seongnam-si, Gyeonggi-do (KR)

(72) Inventor: Jung Joo Lee, Seoul (KR)

(73) Assignee: LIVSMED INC., Seongnam-si, Gyeonggi-Do (KR)

( * ) Notice: Subject to any disclaimer, the term of this patent is extended or adjusted under 35 U.S.C. 154(b) by 291 days.

(21) Appl. No.: 14/360,589

(22) PCT Filed: Nov. 8, 2012

(86) PCT No.: PCT/KR2012/009365
§ 371 (c)(1),
(2) Date: May 23, 2014

(87) PCT Pub. No.: WO2013/077572
PCT Pub. Date: May 30, 2013

(65) Prior Publication Data
US 2014/0318288 A1    Oct. 30, 2014

(30) Foreign Application Priority Data
Nov. 23, 2011   (KR) .......................... 10-2011-0123072

(51) Int. Cl.
*F16H 19/06*     (2006.01)
*A61B 17/29*     (2006.01)
*A61B 34/00*     (2016.01)

(52) U.S. Cl.
CPC ............. *F16H 19/06* (2013.01); *A61B 17/29* (2013.01); *A61B 17/2909* (2013.01); *A61B 34/71* (2016.02); *A61B 34/70* (2016.02); *A61B 2017/2902* (2013.01); *A61B 2017/2911* (2013.01); *A61B 2017/2927* (2013.01); *Y10T 74/18056* (2015.01); *Y10T 74/18832* (2015.01)

(58) Field of Classification Search
CPC ...... F16H 19/06; F16H 19/0618; F16H 19/08; A61B 17/06; A61B 17/29; A61B 17/2909; A61B 2017/2902; A61B 2017/2911; A61B 2017/2927; A61B 2017/1903; A61B 2017/2924
See application file for complete search history.

(56) References Cited

U.S. PATENT DOCUMENTS

| | | | | |
|---|---|---|---|---|
| 3,273,408 A | * | 9/1966 | Nagel | B23Q 1/4804 400/322 |
| 3,529,481 A | * | 9/1970 | Budzyn | B23Q 1/621 108/21 |
| 5,539,987 A | * | 7/1996 | Zennyoji | F16H 19/06 33/1 M |

(Continued)

FOREIGN PATENT DOCUMENTS

| | | |
|---|---|---|
| CN | 102131469 A | 7/2011 |
| JP | S64-49739 A | 2/1989 |

(Continued)

*Primary Examiner* — David M Fenstermacher
(74) *Attorney, Agent, or Firm* — Novick, Kim & Lee, PLLC; Sang Ho Lee

(57) ABSTRACT

Provided is a differential member that is used in a surgical instrument, which may be manually operated to perform laparoscopic operations or various surgical operations, to receive an input of two or more rotation motions or translation motions and output a single rotation motion or translation motion.

31 Claims, 19 Drawing Sheets

(56) References Cited

U.S. PATENT DOCUMENTS

| | | | |
|---|---|---|---|
| 5,792,165 A | 8/1998 | Klieman et al. | |
| 5,954,731 A | 9/1999 | Yoon | |
| 2006/0190034 A1* | 8/2006 | Nishizawa | A61B 17/29 606/205 |
| 2007/0208375 A1 | 9/2007 | Nishizawa et al. | |
| 2008/0000317 A1* | 1/2008 | Patton | A61F 5/0102 74/500.5 |
| 2008/0039255 A1* | 2/2008 | Jinno | A61B 17/062 474/148 |
| 2008/0245175 A1 | 10/2008 | Jinno et al. | |
| 2009/0112230 A1 | 4/2009 | Jinno | |
| 2010/0198253 A1* | 8/2010 | Jinno | A61B 17/29 606/205 |
| 2010/0249818 A1* | 9/2010 | Jinno | A61B 17/29 606/174 |
| 2013/0012959 A1* | 1/2013 | Jinno | A61B 17/29 606/130 |

FOREIGN PATENT DOCUMENTS

| | | |
|---|---|---|
| JP | 2006-116194 A | 5/2006 |
| JP | 4701433 B2 | 3/2011 |
| KR | 10-2006-0093060 A | 8/2006 |
| KR | 10-0695471 B1 | 3/2007 |
| WO | 2009158115 A1 | 12/2009 |

* cited by examiner

DIFFERENTIAL MEMBER

TECHNICAL FIELD

The present invention relates to differential members, and more particularly, to a differential member that is used in a surgical instrument, which may be manually operated to perform laparoscopic operations or various surgical operations, to receive an input of two or more rotation motions or translation motions and output a single rotation motion or translation motion.

BACKGROUND ART

A surgical operation is an operation for curing a disease by cutting, incising, and processing skin, membranes, or other tissues by using medical instruments. However, open surgery, which cuts and opens the skin of a surgical region and cures, shapes, or removes an organ therein, may cause bleeding, side effects, pain, scars, or the like. Therefore, a surgical operation, which is performed by forming a hole through the skin and inserting a medical instrument, for example, a laparoscope, a surgical instrument, or a surgical microscope thereinto, or a robotic surgical operation have recently become popular alternatives.

The surgical instrument is an instrument for performing, by a surgeon, an operation on a surgical region by operating an end tool, which is installed at one end of a shaft inserted into a hole formed through the skin, by using an operator or by using a robotic arm. The end tool provided in the surgical instrument performs a rotating operation, a gripping operation, a cutting operation, or the like through a predetermined structure.

However, since a conventional surgical instrument uses an unbendable end tool, it is not suitable for accessing a surgical region and performing various surgical operations. In order to solve this problem, a surgical instrument having a bendable end tool has been developed. However, an operation of an operator for bending the end tool to perform a surgical operation is not intuitively identical to an actual bending operation of the end tool for performing the surgical operation. Therefore, for surgical operators, it is difficult to perform an intuitive operation, and it takes a long time to learn how to use the surgical instrument.

Information disclosed in this Background section was already known to the inventors of the present invention before achieving the present invention or is technical information acquired in the process of achieving the present invention. Therefore, it may contain information that does not form the prior art that is already known in this country to a person of ordinary skill in the art.

DETAILED DESCRIPTION OF THE INVENTION

Technical Problem

The present invention provides a differential member that is used in a surgical instrument, which may be manually operated to perform laparoscopic operations or various surgical operations, to receive an input of two or more rotation motions or translation motions and output a single rotation motion or translation motion.

Technical Solution

According to an aspect of the present invention, there is provided a differential member including two or more input units each receiving an input of an amount of rotation motion or translation motion from outside; and an output unit outputting a single rotation motion or translation motion based on rotation motions or translation motions input to the two or more input units.

Advantageous Effects

According to the present invention, it is possible to accurately extract a desired output from a plurality of inputs in a surgical instrument or the like by receiving an input of two or more rotation motions or translation motions and outputting a single rotation motion or translation motion just by a mechanical structure.

BEST MODE

Figure 1:
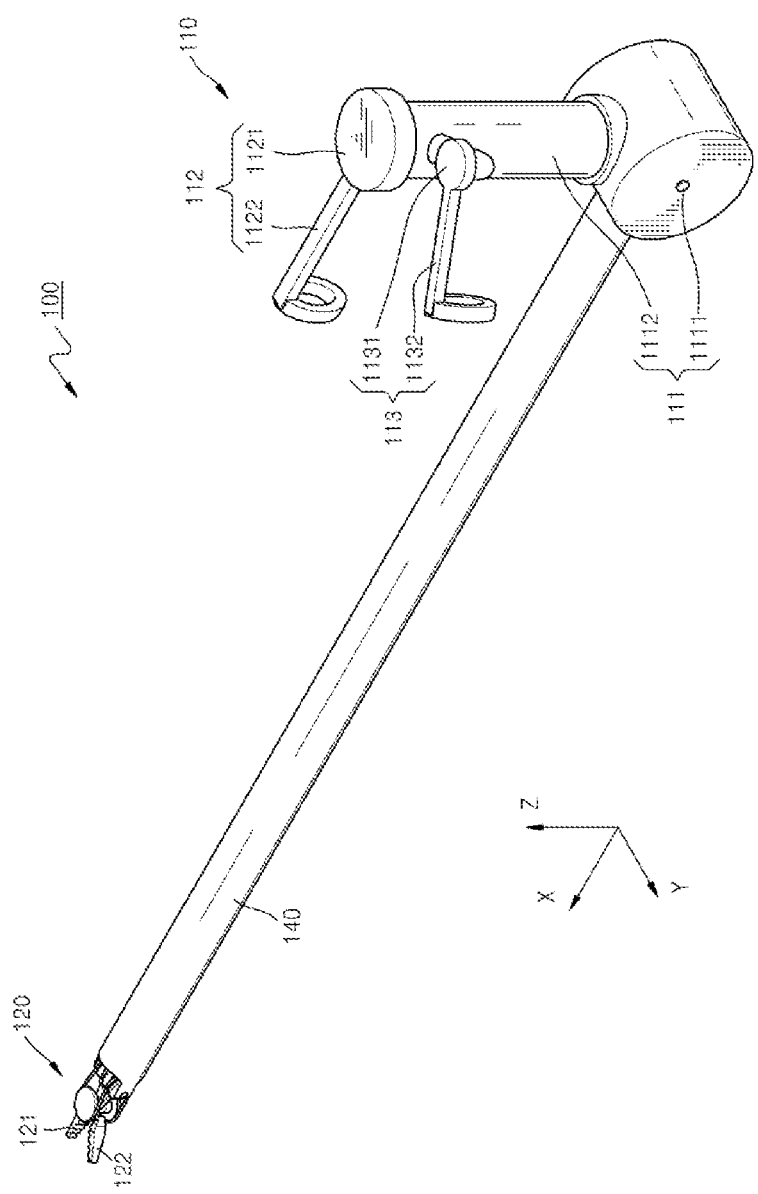
FIG. 1 is a view illustrating a surgical instrument according to a first embodiment of the present invention.

The present invention may include various embodiments and modifications, and exemplary embodiments thereof are illustrated in the drawings and will be described herein in detail. However, it will be understood that the present invention is not limited to the exemplary embodiments and includes all modifications, equivalents and substitutions falling within the spirit and scope of the present invention. In the following description, detailed descriptions of well-known functions or configurations will be omitted since they would unnecessarily obscure the subject matters of the present invention.

Although terms such as "first" and "second" may be used herein to describe various elements or components, these elements or components should not be limited by these terms. These terms are only used to distinguish one element or component from another element or component.

The terminology used herein is for the purpose of describing particular embodiments only and is not intended to be limiting of the inventive concept. As used herein, the singular forms "a", "an", and "the" are intended to include the plural forms as well, unless the context clearly indicates otherwise. It will be understood that terms such as "comprise", "include", and "have", when used herein, specify the presence of stated features, integers, steps, operations, elements, components, or combinations thereof, but do not preclude the presence or addition of one or more other features, integers, steps, operations, elements, components, or combinations thereof.

Hereinafter, embodiments of the present invention will be described in detail with reference to the accompanying drawings. In the following description, like reference numerals denote like elements, and redundant descriptions thereof will be omitted.

Also, it will be understood that various embodiments of the present invention may be interpreted or implemented in combination, and technical features of each embodiment may be interpreted or implemented in combination with technical features of other embodiments.

<First Embodiment of Surgical Instrument> (E3+H1+D3)

Figure 2:
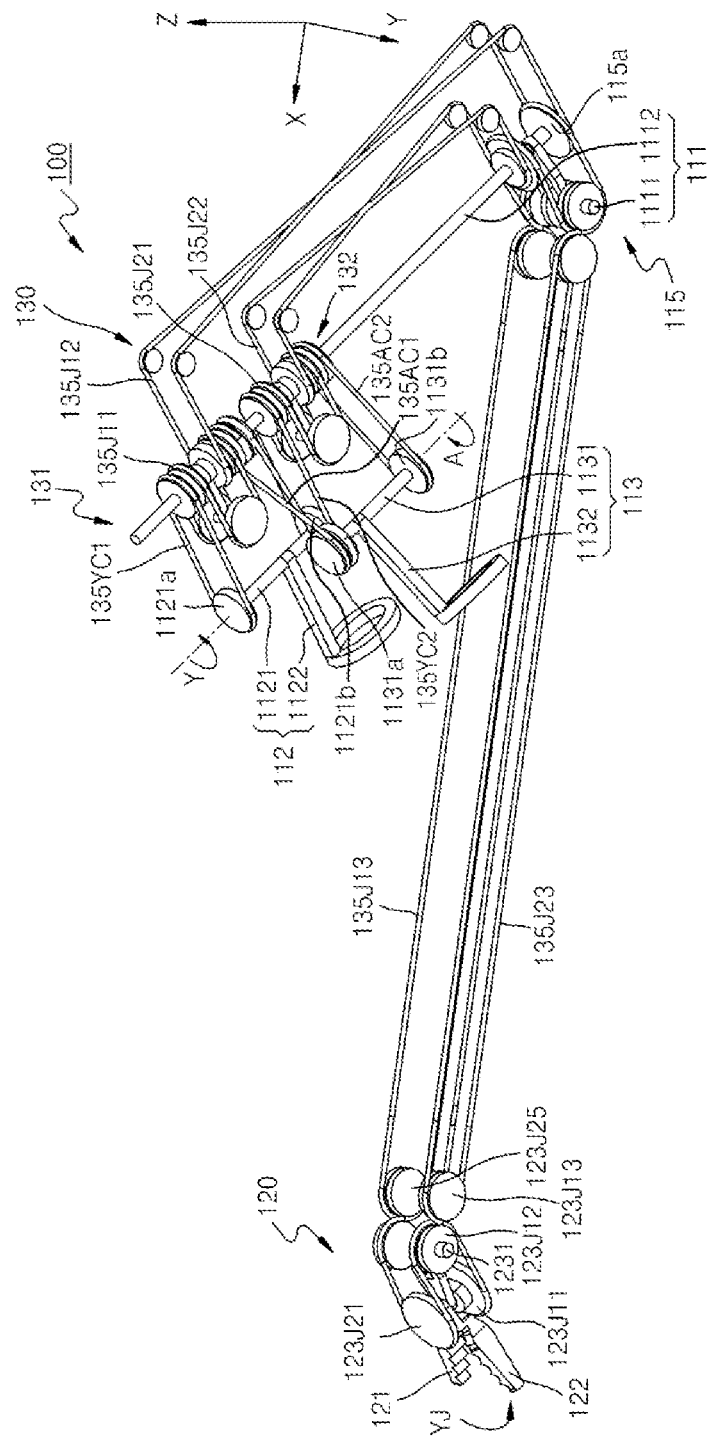
FIG. 2 is a detailed internal view of the surgical instrument of FIG. 1.

FIG. 1 is a view illustrating a surgical instrument 100 according to a first embodiment of the present invention, and FIG. 2 is a detailed internal view of the surgical instrument 100 of FIG. 1.

Referring to FIGS. 1 and 2, the surgical instrument 100 according to a first embodiment of the present invention includes an operator 110, an end tool 120, an operating force transmitter 130, and a connector 140. Herein, the connector 140 may be formed to have a shape of a hollow shaft, so that one or more wires (which will be described later) may be accommodated therein. The operator 110 may be coupled to one end portion of the connector 140, and the end tool 120 may be coupled to the other end portion of the connector 140, so that the connector 140 may connect the operator 110 and the end tool 120.

In detail, the operator 110 is formed at one end portion of the connector 140 and is provided as an interface having, for example, a tweezers shape, a stick shape, or a lever shape, which may be directly operated by a surgical operator. When a surgical operator operates the operator 110, the end tool 120, which is connected to the interface and is inserted into the body of a surgical patient, performs an operation, thereby performing a surgical operation. Although FIG. 1 illustrates that the operator 110 is formed to have a tweezers shape, the present invention is not limited thereto, and the operator 110 may have various shapes that may be connected with the end tool 120 to operate the end tool 120.

The end tool 120 is formed at the other end portion of the connector 140 and is inserted into a surgical region to perform a necessary surgical operation. As an example of the end tool 120, a pair of jaws, namely, first and second jaws 121 and 122, may be used to perform a grip operation, as illustrated in FIG. 1. However, the present invention is not limited thereto, and various surgical devices may be used as the end tool 120. For example, a one-armed cautery may be used as the end tool 120. The end tool 120 is connected with the operator 110 by the operating force transmitter 130 to receive an operating force of the operator 110 through the operating force transmitter 130, thereby performing a necessary surgical operation such as a grip, cutting, or suturing. Herein, the end tool 120 of the surgical instrument 100 according to the first embodiment of the present invention is formed to rotate in two or more directions. For example, the end tool 120 may be formed to perform a pitch motion around a Y axis of FIG. 1 and also perform a yaw motion and an actuation motion around a Z axis of FIG. 1. This will be described later in detail.

The operating force transmitter 130 connects the operator 110 and the end tool 120 to transmit an operating force of the operator 110 to the end tool 120 and may include a plurality of wires and pulleys.

Hereinafter, the operator 110, the end tool 120, and the operating force transmitter 130 of the surgical instrument 100 of FIG. 1 will be described in more detail.

(Operator)

Figure 3:
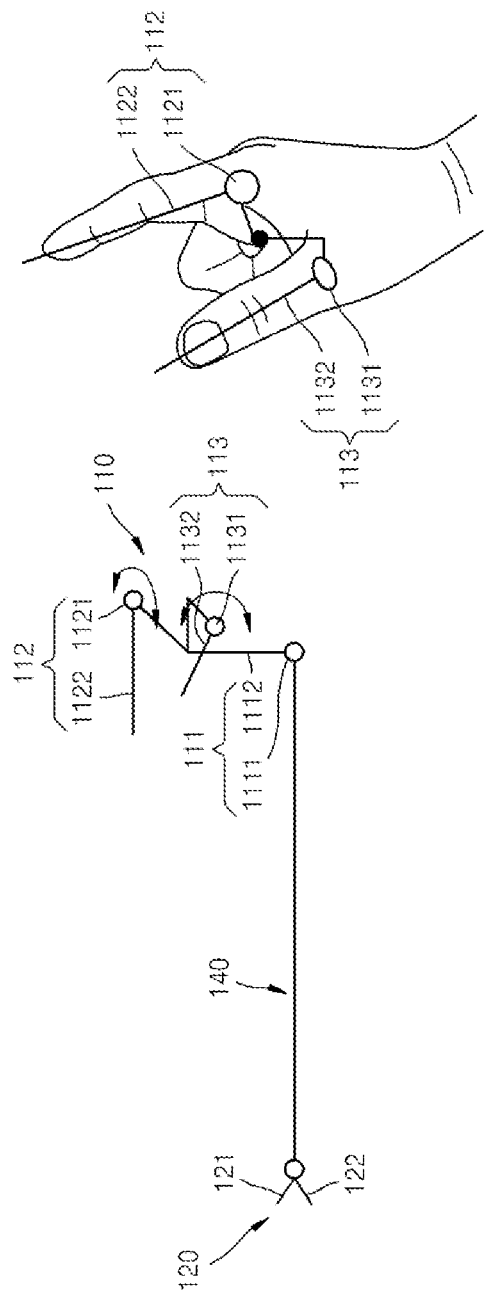
FIG. 3 is a schematic view of an operator of the surgical instrument of FIG. 2.

FIG. 3 is a schematic view of an operator 110 of the surgical instrument 100 of FIG. 2.

Referring to FIGS. 1, 2, and 3, the operator 110 of the surgical instrument 100 according to the first embodiment of the present invention includes a pitch operator 111 controlling a pitch motion of the end tool 120, a yaw operator 112 controlling a yaw motion of the end tool 120, and an actuation operator 113 controlling an actuation motion of the end tool 120.

A pitch operation, a yaw operation, and an actuation operation used in the present invention are summarized as follows:

First, the pitch operation refers to a vertical motion with respect to an extension direction (an X-axis direction of FIG. 1) of the connector 140, that is, an operation of rotating around the Y axis of FIG. 1. In other words, the pitch operation refers to a vertical rotation of the end tool 120, which is formed to extend in the extension direction (the X-axis direction of FIG. 1) of the connector 140, around the Y axis. The yaw operation refers to a horizontal motion with respect to the extension direction (the X-axis direction of FIG. 1) of the connector 140, that is, an operation of rotating around the Z axis of FIG. 1. In other words, the yaw operation refers to a horizontal rotation of the end tool 120, which is formed to extend in the extension direction (the X-axis direction of FIG. 1) of the connector 140, around the Z axis. The actuation operation refers a folding or unfolding operation of the first and second jaws 121 and 122 when the first and second jaws 121 and 122 rotate in opposite directions while rotating around the same rotating axis as the yaw operation. That is, the actuation operation refers to rotations of the first and second jaws 121 and 122, which is formed at the end tool 120, in opposite directions around the Z axis.

Herein, when the operator 110 of the surgical instrument 100 is rotated in one direction, the end tool 120 rotates in a direction that is intuitively identical to an operation direction of the operator 110. In other words, when the pitch operator 111 of the operator 110 rotates in one direction, the end tool 120 rotates in a direction intuitively identical to the one direction to perform a pitch operation, and the end tool 120 rotates in the direction intuitively identical to the one direction to perform a yaw operation. Herein, it may be said that the intuitively identical direction refers to a case where a movement direction of an index finger of a user gripping the operator 110 is substantially identical to a movement direction of the end portion of the end tool 120. In addition, the identical direction may not be an exactly identical direction on a three-dimensional coordinate system. For example, the identical direction may refer to a case where when the index finger of the user moves to the left, the end portion of the end tool 120 also moves to the left, and when the index finger of the user moves to the right, the end portion of the end tool 120 also moves to the right.

To this end, in the surgical instrument 100, the operator 110 and the end tool 120 are formed in the same direction with respect to a plane perpendicular to an extension axis (X axis) of the connector 140. That is, in view of a YZ plane of FIG. 1, the operator 110 is formed to extend in a +X-axis direction, and the end tool 120 is also formed to extend in the +X-axis direction. In other words, it may be said that a formation direction of the end tool 120 at one end portion of the connector 140 may be identical to a formation direction of the operator 110 at the other end portion of the connector 140 in view of the YZ plane. In other words, it may be said that the operator 110 is formed to extend away from a body of the user gripping the operator 110, that is, the operator 110 is formed to extend toward the end tool 120.

In detail, in the case of a surgical instrument of the related art, an operation direction of an operator by a user is different from and is not intuitively identical to an actual operation direction of an end tool. Therefore, a surgical operator has difficulty in performing an intuitive operation and it takes a long time to skillfully move the end tool in a desired direction. Also, in some cases, a faulty operation may occur, thus damaging a surgical patient.

In order to solve such problems, the surgical instrument 100 according to the first embodiment of the present invention is configured such that an operation direction of the operator 110 is intuitively identical to an operation direction of the end tool 120. To this end, the operator 110 and the end tool 120 are formed on the same side in view of the YZ plane including a pitch operating axis 1111. This will be described below in more detail.

Referring to FIGS. 1, 2, and 3, the operator 110 of the surgical instrument 100 according to the first embodiment of the present invention includes the pitch operator 111 controlling a pitch motion of the end tool 120, a yaw operator 112 controlling a yaw motion of the end tool 120, and an actuation operator 113 controlling an actuation motion of the end tool 120.

The pitch operator 111 includes the pitch operating axis 1111 and a pitch operating bar 1112. Herein, the pitch operating axis 1111 may be formed in a direction parallel to the Y axis, and the pitch operating bar 1112 may be connected with the pitch operating axis 1111 to rotate along with the pitch operating axis 1111. For example, when the user grips and rotates the pitch operating bar 1112, the pitch operating axis 1111 connected with the pitch operating bar 1112 rotates along with the pitch operating bar 1112. Then, the resulting rotating force is transmitted to the end tool 120 through the operating force transmitter 130, so that the end tool 120 rotates in the same direction as the rotation direction of the pitch operating axis 1111. That is, when the pitch operator 111 rotates in the clockwise direction around the pitch operating axis 1111, the end tool 120 also rotates in the clockwise direction around an axis parallel to the pitch operating axis 1111, and when the pitch operator 111 rotates in the counterclockwise direction around the pitch operating axis 1111, the end tool 120 also rotates in the counterclockwise direction around the axis parallel to the pitch operating axis 1111.

The yaw operator 112 and the actuation operator 113 are formed on one end portion of the pitch operating bar 1112 of the pitch operator 111. Thus, when the pitch operator 111 rotates around the pitch operating axis 1111, the yaw operator 112 and the actuation operator 113 also rotate along with the pitch operator 111. FIGS. 1 and 3 illustrate a state in which the pitch operating bar 1112 of the pitch operator 111 is perpendicular to the connector 140, while FIG. 2 illustrates a state in which the pitch operating bar 1112 of the pitch operator 111 is at an angle to the connector 140.

Therefore, a coordinate system of the yaw operator 112 and the actuation operator 113 is not fixed, but relatively changes according to the rotation of the pitch operator 111. As illustrated in FIG. 1, since a yaw operating axis 1121 of the yaw operator 112 and an actuation operating axis 1131 of the actuation operator 113 are parallel to the Z axis, the yaw operator 112 and the actuation operator 113 rotate around an axis parallel to the Z axis. However, as illustrated in FIG. 2, when the pitch operator 111 rotates, the yaw operating axis 1121 of the yaw operator 112 and the actuation operating axis 1131 of the actuation operator 113 are not parallel to the Z axis. That is, the coordinate system of the yaw operator 112 and the actuation operator 113 change according to the rotation of the pitch operator 111. However, for convenience of description, the coordinate system of the yaw operator 112 and the actuation operator 113 will be described on the assumption that the pitch operating bar 1112 is perpendicular to the connector 140 as illustrated in FIG. 1.

The yaw operator 112 includes the yaw operating axis 1121 and a yaw operating bar 1122. Herein, the yaw operating axis 1121 may be formed to be at a predetermined angle to an XY plane where the connector 140 is formed. For example, the yaw operating axis 1121 may be formed in a direction parallel to the Z axis as illustrated in FIG. 1, and when the pitch operator 111 rotates, the coordinate system of the yaw operator 112 may relatively change as described above. However, the present invention is not limited thereto, and the yaw operating axis 1121 may be formed in various directions by ergonomic design according to the structure of a hand of the user gripping the yaw operator 112. The yaw operating bar 1122 is connected with the yaw operating axis 1121 to rotate along with the yaw operating axis 1121. For example, when the user holds and rotates the yaw operating bar 1122 with the index finger, the yaw operating axis 1121 connected with the yaw operating bar 1122 rotates along with the yaw operating bar 1122. Then, the resulting rotating force is transmitted to the end tool 120 through the operating force transmitter 130, so that the first and second jaws 121 and 122 of the end tool 120 horizontally rotate in the same direction as the rotation direction of the yaw operating axis 1121.

A first pulley 1121a and a second pulley 1121b may be formed respectively at both end portions of the yaw operating axis 1121. A YC1 wire 135YC1 may be connected to the first pulley 1121a, and a YC2 wire 135YC2 may be connected to the second pulley 1121b.

The actuation operator 113 includes the actuation operating axis 1131 and an actuation operating bar 1132. Herein, the actuation operating axis 1131 may be formed to be at a predetermined angle to the XY plane where the connector 140 is formed. For example, the actuation operating axis 1131 may be formed in a direction parallel to the Z axis as illustrated in FIG. 1, and when the pitch operator 111 rotates, the coordinate system of the actuation operator 113 may relatively change as described above. However, the present invention is not limited thereto, and the actuation operating axis 1131 may be formed in various directions by ergonomic design according to the structure of the hand of the user gripping the actuation operator 113. The actuation operating bar 1132 is connected with the actuation operating axis 1131 to rotate along with the actuation operating axis 1131. For example, when the user holds and rotates the actuation operating bar 1132 with the thumb finger, the actuation operating axis 1131 connected with the actuation operating bar 1132 rotates along with the actuation operating bar 1132. Then, the resulting rotating force is transmitted to the end tool 120 through the operating force transmitter 130, so that the first and second jaws 121 and 122 of the end tool 120 perform an actuation operation. Herein, as described above, the actuation operation refers to an operation of folding or unfolding the first and second jaws 121 and 122 by rotating the first and second jaws 121 and 122 in opposite directions. That is, when the actuation operator 113 is rotated in one direction, as the first jaw 121 rotates in the counterclockwise direction and the second jaw 122 rotates in the clockwise direction, the end tool 120 is folded; and when the actuation operator 113 is rotated in the opposite direction, as the first jaw 121 rotates in the clockwise direction and the second jaw 122 rotates in the counterclockwise direction, the end tool 120 is unfolded.

A first pulley 1131a and a second pulley 1131b may be formed respectively at both end portions of the actuation operating axis 1131. An AC1 wire 135AC1 may be connected to the first pulley 1131a, and an AC2 wire 135AC2 may be connected to the second pulley 1131b.

Referring to FIG. 3, the pitch operator 111 and the end tool 120 are formed on the same or parallel axis (X axis) in the surgical instrument 100 according to the first embodiment of the present invention. That is, the pitch operating axis 1111 of the pitch operator 111 is formed at one end portion of the connector 140, and the end tool 120 is formed at the other end portion of the connector 140. Although it is illustrated that the connector 140 is formed to have the shape of a straight line, the present invention is not limited thereto. For example, the connector 140 may be curved with a predetermined curvature, or may be bent one or more times. Also in this case, it may be said that the pitch operator 111 and the end tool 120 are formed on substantially the same or parallel axis. Although FIG. 3 illustrates that the pitch operator 111 and the end tool 120 are formed on the same axis (X axis), the present invention is not limited thereto. For example, the pitch operator 111 and the end tool 120 may be formed on different axes. This will be described later in detail.

The operator 110 of the surgical instrument 100 according to the first embodiment of the present invention further includes an operator control member 115 engaged with the pitch operating axis 1111 of the pitch operator 111. The operator control member 115 may include a relay pulley 115a. Since the configuration of the operator control member 115 is substantially identical to the configuration of the end tool 120, the relations between the operator control member 115 and other elements of the operator 110 and an end tool control member 123 will be described later.

Figure 3A:
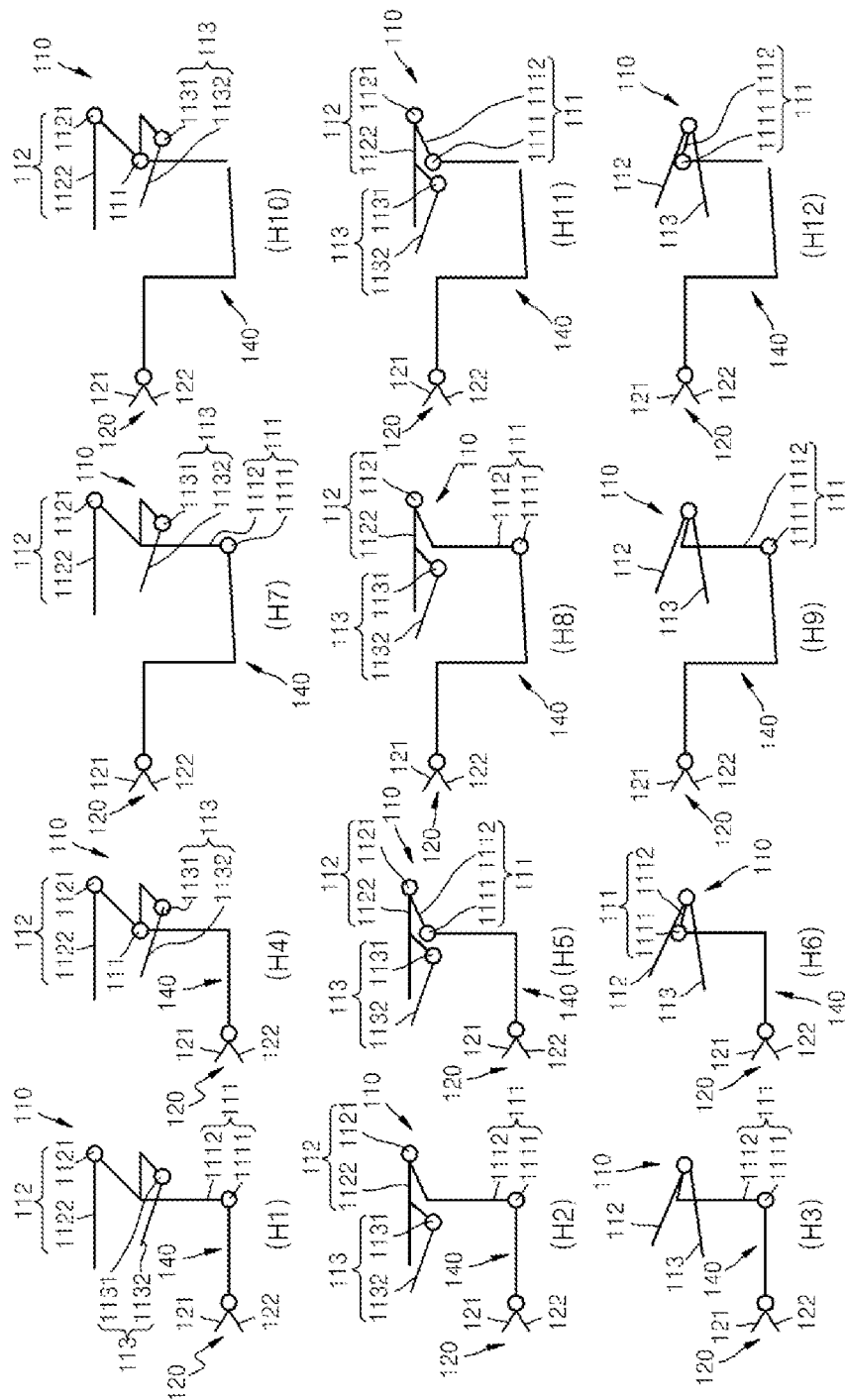
FIG. 3A illustrates various modifications of the operator of the surgical instrument according to the first embodiment of the present invention.

FIG. 3A illustrates various modifications of the operator 110 of the surgical instrument 100 according to the first embodiment of the present invention.

As for H1 of FIG. 3A, as described with reference to FIG. 3, (1) since the yaw operator 112 and the actuation operator 113 of the operator 110 are formed independently of each other, the rotation of one of the yaw operator 112 and the actuation operator 113 does not affect the rotation of the other of the yaw operator 112 and the actuation operator 113, (2) the pitch operator 111 is disposed under the plane formed by the yaw operator 112 and the actuation operator 113, and (3) the yaw operator 112 and the actuation operator 113 are formed over an extension line of the end tool 120. H1 may be seen in the first, fourth, and seventh embodiments of the present invention.

As for H2 of FIG. 3A, (1) since the actuation operator 113 of the operator 110 is formed on the yaw operator 112, when the yaw operator 112 rotates, the actuation operator 113 also rotates, (2) the pitch operator 111 is disposed under the plane formed by the yaw operator 112 and the actuation operator 113, and (3) the yaw operator 112 and the actuation operator 113 are formed over the extension line of the end tool 120. H2 may be seen in the second, fifth, and eighth embodiments of the present invention.

As for H3 of FIG. 3A, (1) a first jaw operator 112 and a second jaw operator 113, which rotate independently of each other, are formed in the operator 110, (2) the pitch operator 111 is disposed under the plane formed by the yaw operator 112 and the actuation operator 113, and (3) the yaw operator 112 and the actuation operator 113 are formed over the extension line of the end tool 120. H3 may be seen in the third, sixth, and ninth embodiments of the present invention.

As for H4 of FIG. 3A, (1) since the yaw operator 112 and the actuation operator 113 of the operator 110 are formed independently of each other, the rotation of one of the yaw operator 112 and the actuation operator 113 does not affect the rotation of the other of the yaw operator 112 and the actuation operator 113, (2) the pitch operator 111 is disposed on a plane identical to or adjacent to the plane formed by the yaw operator 112 and the actuation operator 113 such that the pitch operator 111 is more adjacent to the yaw operator 112 and the actuation operator 113, as compared to H1 case, and (3) the yaw operator 112 and the actuation operator 113 are formed over the extension line of the end tool 120. H4 may be seen in detail in FIG. 9.

As for H5 of FIG. 3A, (1) since the actuation operator 113 of the operator 110 is formed on the yaw operator 112, when the yaw operator 112 rotates, the actuation operator 113 also rotates, (2) the pitch operator 111 is disposed on a plane identical to or adjacent to the plane formed by the yaw operator 112 and the actuation operator 113 such that the pitch operator 111 is more adjacent to the yaw operator 112 and the actuation operator 113, as compared to H2 case, and (3) the yaw operator 112 and the actuation operator 113 are formed over the extension line of the end tool 120.

As for H6 of FIG. 3A, (1) a first jaw operator 112 and a second jaw operator 113, which rotate independently of each other, are formed in the operator 110, (2) the pitch operator 111 is disposed on a plane identical to or adjacent to the plane formed by the yaw operator 112 and the actuation operator 113 such that the pitch operator 111 is more adjacent to the yaw operator 112 and the actuation operator 113, as compared to the H3 case, and (3) the yaw operator 112 and the actuation operator 113 are formed over the extension line of the end tool 120.

As for H7 of FIG. 3A, (1) since the yaw operator 112 and the actuation operator 113 of the operator 110 are formed independently of each other, the rotation of one of the yaw operator 112 and the actuation operator 113 does not affect the rotation of the other of the yaw operator 112 and the actuation operator 113, (2) the pitch operator 111 is disposed under the plane formed by the yaw operator 112 and the actuation operator 113, and (3) the yaw operator 112 and the actuation operator 113 are formed on the extension line of the end tool 120.

As for H8 of FIG. 3A, (1) since the actuation operator 113 of the operator 110 is formed on the yaw operator 112, when the yaw operator 112 rotates, the actuation operator 113 also rotates, (2) the pitch operator 111 is disposed under the plane formed by the yaw operator 112 and the actuation operator 113, and (3) the yaw operator 112 and the actuation operator 113 are formed on the extension line of the end tool 120.

As for H9 of FIG. 3A, (1) a first jaw operator 112 and a second jaw operator 113, which rotate independently of each other, are formed in the operator 110, (2) the pitch operator 111 is disposed under the plane formed by the yaw operator 112 and the actuation operator 113, and (3) the yaw operator 112 and the actuation operator 113 are formed on the extension line of the end tool 120.

As for H10 of FIG. 3A, (1) since the yaw operator 112 and the actuation operator 113 of the operator 110 are formed independently of each other, the rotation of one of the yaw operator 112 and the actuation operator 113 does not affect the rotation of the other of the yaw operator 112 and the actuation operator 113, (2) the pitch operator 111 is disposed on a plane identical to or adjacent to the plane formed by the yaw operator 112 and the actuation operator 113 such that the pitch operator 111 is more adjacent to the yaw operator 112 and the actuation operator 113, as compared to the H7 case, and (3) the yaw operator 112 and the actuation operator 113 are formed on the extension line of the end tool 120.

As for H11 of FIG. 3A, (1) since the actuation operator 113 of the operator 110 is formed on the yaw operator 112, when the yaw operator 112 rotates, the actuation operator 113 also rotates, (2) the pitch operator 111 is disposed on a plane identical to or adjacent to the plane formed by the yaw operator 112 and the actuation operator 113 such that the pitch operator 111 is more adjacent to the yaw operator 112 and the actuation operator 113, as compared to the H8 case, and (3) the yaw operator 112 and the actuation operator 113 are formed on the extension line of the end tool 120.

As for H12 of FIG. 3A, (1) a first jaw operator 112 and a second jaw operator 113, which rotate independently of each other, are formed in the operator 110, (2) the pitch operator 111 is disposed on a plane identical to or adjacent to the plane formed by the yaw operator 112 and the actuation operator 113 such that the pitch operator 111 is more adjacent to the yaw operator 112 and the actuation operator 113, as compared to the H9 case, and (3) the yaw operator 112 and the actuation operator 113 are formed on the extension line of the end tool 120.

In addition to the above modifications, various other modifications of the operator 110 may be applicable to the surgical instrument of the present invention.

(Operating Force Transmitter)

Figure 4A:
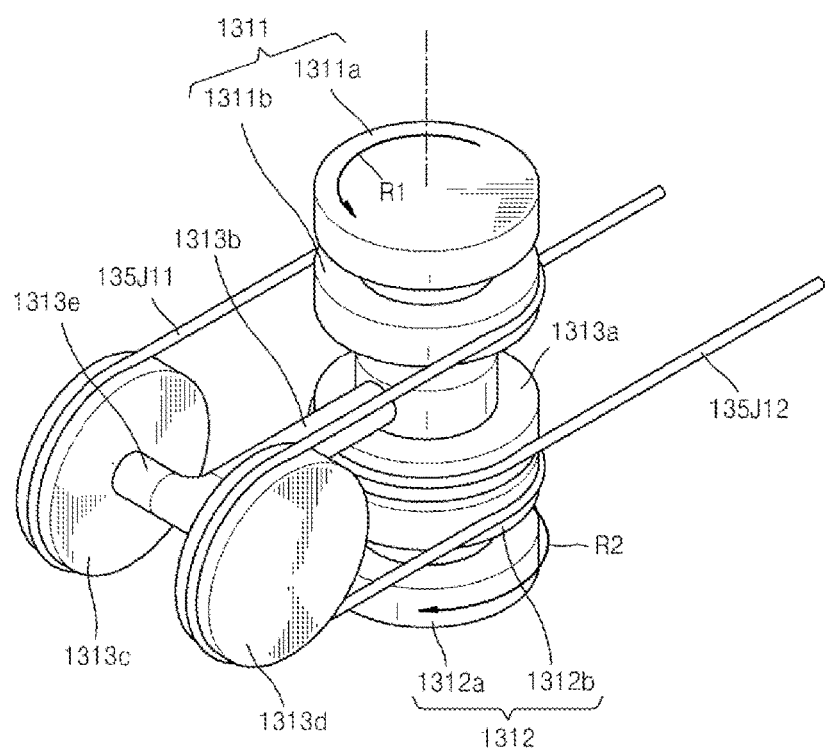
FIG. 4A is a detailed view of a first differential pulley of the surgical instrument of FIG. 2.
Figure 4B:
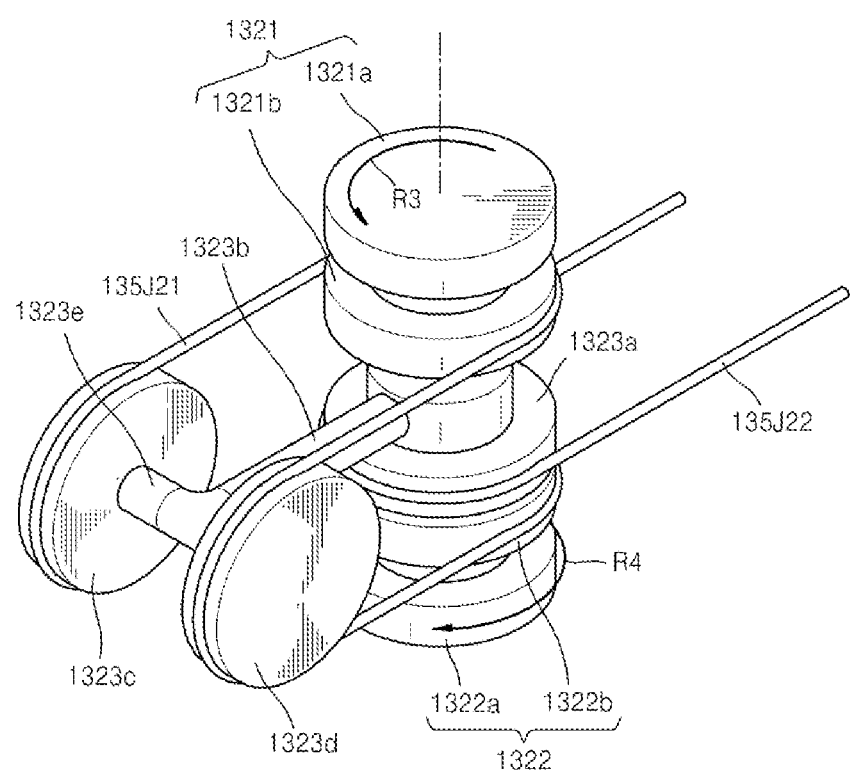
FIG. 4B is a detailed view of a second differential pulley of the surgical instrument of FIG. 2.

FIG. 4A is a detailed view of a first differential pulley 131 of the surgical instrument 100 of FIG. 2, and FIG. 4B is a detailed view of a second differential pulley 132 of the surgical instrument 100 of FIG. 2.

Referring to FIGS. 1, 2, 4A, and 4B, the operating force transmitter 130 of the surgical instrument 100 according to the first embodiment of the present invention includes first and second differential pulleys 131 and 132, a plurality of pulleys, and a plurality of wires 135YC1, 135YC2, 135J11, 135J12, 135J13, 135J21, 135J22, and 135J23. Although it is illustrated that the first and second differential pulleys 131 and 132 include a plurality of pulleys, the present invention is not limited thereto, and a differential member including a differential pulley and a differential gear according to the present invention may include various types of rotating bodies.

First, the first differential pulley 131 of the operating force transmitter 130 will be described below.

As described above, the yaw operator 112 and the actuation operator 113 are formed on one end portion of the pitch operating bar 1112 of the pitch operator 111. Thus, when the pitch operator 111 rotates around the pitch operating axis 1111, the yaw operator 112 and the actuation operator 113 also rotate along with the pitch operator 111. Also, the yaw operator 112 is connected with the first jaw 121 and the second jaw 122 to operate the first jaw 121 and the second jaw 122, and the actuation operator 113 is connected with the first jaw 121 and the second jaw 122 to operate the first jaw 121 and the second jaw 122. However, when the yaw operator 112 is rotated, the first jaw 121 and the second jaw 122 have to rotate in the same direction; and when the actuation operator 113 is rotated, the first jaw 121 and the second jaw 122 have to rotate in opposite directions. In order to implement this operation, a separate structure is required.

Thus, two rotation inputs of the yaw operator 112 and the actuation operator 113 have to be applied to one jaw. Accordingly, a structure for receiving two or more inputs and outputting a rotation of one jaw is required. In this case, two rotation inputs have to be independent of each other.

To this end, the surgical instrument 100 according to the first embodiment of the present invention includes a differential member including two or more input units and one output unit to receive an input of rotating forces from two or more input units from the two input units, extract a desired rotating force through the sum of or the difference between the two rotating forces, and output the desired rotating force through the output unit. The differential member may include a differential pulley using pulleys and wires, and a differential gear using gears, and a differential pulley is illustrated as an example of the differential member in FIGS. 1, 2, 4A, and 4B. Various embodiments of the differential member are illustrated in FIGS. 7 to 19.

In detail, the first differential pulley 131 includes a first input unit 1311, a second input unit 1312, and an output unit 1313.

The first input unit 1311 includes a first pulley 1311a and a second pulley 1311b. The first pulley 1311a and the second pulley 1311b rotate together around the same rotating axis. Herein, the first pulley 1311a of the first input unit 1311 is connected with the first pulley 1121a of the yaw operator 112 by the YC1 wire 135YC1 to transmit a rotation of the yaw operator 112 to the first input unit 1311. Also, the second pulley 1311b of the first input unit 1311 is connected with the output unit 1313 by the differential control wire 135J11 to transmit a rotation of the first input unit 1311 to the output unit 1313.

The second input unit 1312 includes a first pulley 1312a and a second pulley 1312b. The first pulley 1312a and the second pulley 1312b rotate together around the same rotating axis. Herein, the first pulley 1312a of the second input unit 1312 is connected with the first pulley 1131a of the actuation operator 113 by the AC1 wire 135AC1 to transmit a rotation of the actuation operator 113 to the second input unit 1312. Also, the second pulley 1312b of the second input unit 1312 is connected with the output unit 1313 by the differential control wire 135J11 to transmit a rotation of the second input unit 1312 to the output unit 1313.

The output unit 1313 includes an output pulley 1313a, an extension portion 1313b, a first differential control pulley 1313c, and a second differential control pulley 1313d.

Herein, the output pulley 1313a of the output unit 1313 is connected with the operator control member 115 by the J12 wire 135J12 to transmit a rotation of the output unit 1313 to the first jaw 121 of the end tool 120 through the operator control member 115. The extension portion 1313b extends in one direction from a rotating axis of the output pulley 1313a to rotate along with the output pulley 1313a. The first differential control pulley 1313c and the second differential control pulley 1313d are formed at one end portion of the extension portion 1313b to face each other and rotate around both end portions of an axis 1313e that is formed at a predetermined angle to the rotating axis of the output pulley 1313a.

Herein, the first input unit 1311, the second input unit 1312, and the output unit 1313 rotate independently around independent axes.

The differential control wire 135J11 is wound along the second pulley 1311b of the first input unit 1311, the first differential control pulley 1313c of the output unit 1313, the second pulley 1312b of the second input unit 1312, and the second differential control pulley 1313d of the output unit 1313 to transmit a rotation of the first input unit 1311 and the second input unit 1312 to the output unit 1313.

Herein, the first differential pulley 131 includes the first input unit 1311, the second input unit 1312, and the output unit 1313, receives an input of amounts of rotation from the first input unit 1311 and the second input unit 1312, and outputs the sum of the amounts of rotation through the output unit 1313. That is, when only the first input unit 1311 rotates, the rotation of the first input unit 1311 is output through the output unit 1313; when only the second input unit 1312 rotates, the rotation of the second input unit 1312 is output through the output unit 1313; when the first input unit 1311 and the second input unit 1312 rotate in the same direction, the sum of the rotations of the first input unit 1311 and the second input unit 1312 is output through the output unit 1313; and when the first input unit 1311 and the second input unit 1312 rotate in opposite directions, the difference between the rotations of the first input unit 1311 and the second input unit 1312 is output through the output unit 1313. This may be expressed as the following equation:

$$C=A+B$$

(where C denotes a rotation of an output unit, A denotes a rotation of a first input unit, and B denotes a rotation of a second input unit.)

The operation of the first differential pulley 131 will be described later in detail.

Like the first differential pulley 131, the second differential pulley 132 includes a first input unit 1321, a second input unit 1322, and an output unit 1323.

Herein, a first pulley 1321a of the first input unit 1321 is connected with the second pulley 1121b of the yaw operator 112 by the YC2 wire 135YC2 to transmit a rotation of the yaw operator 112 to the first input unit 1321. Also, a second pulley 1321b of the first input unit 1321 is connected with the output unit 1323 by a differential control wire 135J21 to transmit a rotation of the first input unit 1321 to the output unit 1323.

A first pulley 1322a of the second input unit 1322 is connected with the second pulley 1131b of the actuation operator 113 by the AC2 wire 135AC2 to transmit a rotation of the actuation operator 113 to the second input unit 1322. Also, the second pulley 1322b of the second input unit 1322 is connected with the output unit 1323 by the differential control wire 135J21 to transmit a rotation of the second input unit 1322 to the output unit 1323.

The output unit 1323 includes an output pulley 1323a, an extension portion 1323b, a first differential control pulley 1323c, and a second differential control pulley 1323d. Herein, the output pulley 1323a of the output unit 1323 is connected with the operator control member 115 by the J22 wire 135J22 to transmit a rotation of the output unit 1323 to the second jaw 122 of the end tool 120 through the operator control member 115.

Herein, the second differential pulley 132 includes the first input unit 1321, the second input unit 1322, and the output unit 1323, receives an input of amounts of rotation from the first input unit 1321 and the second input unit 1322, and outputs the sum of the amounts of rotation through the output unit 1323. That is, when only the first input unit 1321 rotates, the rotation of the first input unit 1321 is output through the output unit 1323; when only the second input unit 1322 rotates, the rotation of the second input unit 1322 is output through the output unit 1323; when the first input unit 1321 and the second input unit 1322 rotate in the same direction, the sum of the rotations of the first input unit 1321 and the second input unit 1322 is output through the output unit 1323; and when the first input unit 1321 and the second input unit 1322 rotate in opposite directions, the difference between the rotations of the first input unit 1321 and the second input unit 1322 is output through the output unit 1323.

The operations of the first differential pulley 131 and the second differential pulley 132 will be described below.

First, a case where only the yaw operator 112 rotates and the actuation operator 113 does not rotate will be described below.

When the yaw operator 112 rotates in the direction of an arrow Y of FIG. 2, the first pulley 1121a of the yaw operator 112, the YC1 wire 135YC1 wound around the first pulley 1121a, the first pulley 1311a of the first input unit 1311 of the first differential pulley 131 around which the YC1 wire 135YC1 is wound, and the second pulley 1311b connected with the first pulley 1311a rotate together. However, the second input unit 1312 of the first differential pulley 131 connected with the actuation operator 113 does not rotate. In this manner, when the first input unit 1311 of the first differential pulley 131 rotates in the direction of an arrow R1 of FIG. 4A and the second input unit 1312 does not rotate, a portion wound around the first input unit 1311 of the differential control wire 135J11 rotates but a portion wound around the second input unit 1312 of the differential control wire 135J11 does not rotate. Accordingly, the wire wound around the second input unit 1312 is unwound as much as the rotation of the portion wound around the first input unit 1311 of the differential control wire 135J11, and the differential control wire 135J11 moves as much. Concurrently, the second differential control pulley 1313d rotates in the clockwise direction, and the first differential control pulley 1313c rotates in the counterclockwise direction. At the same time, the output unit 1313, which includes the output pulley 1313a, the extension portion 1313b, the first differential control pulley 1313c, and the second differential control pulley 1313d, rotates in the direction of the arrow R1 of FIG. 4A around the rotating axis of the output pulley 1313a. Then, the rotation of the output unit 1313 is transmitted to the first jaw 121 of the end tool 120 through the operator control member 115, so that the first jaw 121 rotates in the direction of an arrow YJ of FIG. 2.

Also, when the yaw operator 112 rotates in the direction of the arrow Y of FIG. 2, the second pulley 1121b of the yaw operator 112, the YC2 wire 135YC2 wound around the second pulley 1121b, the first pulley 1321a of the first input unit 1321 of the second differential pulley 132 around which the YC2 wire 135YC2 is wound, and the second pulley 1321*b* connected with the first pulley 1321*a* rotate together. However, the second input unit 1322 of the second differential pulley 132 connected with the actuation operator 113 does not rotate. In this manner, when the first input unit 1321 of the second differential pulley 132 rotates in the direction of an arrow R3 of FIG. 4B and the second input unit 1322 does not rotate, a portion wound around the first input unit 1321 of the differential control wire 135J21 rotates but a portion wound around the second input unit 1322 of the differential control wire 135J21 does not rotate. Accordingly, the wire wound around the second input unit 1322 is unwound as much as the rotation of the portion wound around the first input unit 1321 of the differential control wire 135J21, and the differential control wire 135J21 moves as much. Concurrently, the second differential control pulley 1323*d* rotates in the clockwise direction, and the first differential control pulley 1323*c* rotates in the counterclockwise direction. At the same time, the output unit 1323, which includes the output pulley 1323*a*, the extension portion 1323*b*, the first differential control pulley 1323*c*, and the second differential control pulley 1323*d*, rotates around the rotating axis of the output pulley 1323*a* in the direction of the arrow R3 of FIG. 4B. Then, the rotation of the output unit 1323 is transmitted to the second jaw 122 of the end tool 122 through the operator control member 115, so that the second jaw 122 rotates in the direction of the arrow YJ of FIG. 2.

A case where only the actuation operator 113 rotates and the yaw operator 112 does not rotate will be described below.

When the actuation operator 113 rotates in the direction of an arrow A of FIG. 2, the first pulley 1131*a* of the actuation operator 113, the AC1 wire 135AC1 wound around the first pulley 1131*a*, the first pulley 1312*a* of the second input unit 1312 of the first differential pulley 131 around which the AC1 wire 135AC1 is wound, and the second pulley 1312*b* connected with the first pulley 1312*a* rotate together. Herein, since the AC1 wire 135AC1 is twisted one time, the rotating force of the actuation operator 113 is reversed and transmitted to the first differential pulley 131. However, the first input unit 1311 of the first differential pulley 131 that is connected with the yaw operator 112 does not rotate. In this manner, when the second input unit 1312 of the first differential pulley 131 rotates in a direction opposite to the direction of an arrow R2 of FIG. 4A and the first input unit 1311 does not rotate, a portion wound around the second input unit 1312 of the differential control wire 135J11 rotates but a portion wound around the first input unit 1311 of the differential control wire 135J11 does not rotate. Accordingly, the wire wound around the first input unit 1311 is unwound as much as the rotation of the portion wound around the second input unit 1312 of the differential control wire 135J11, and the differential control wire 135J11 moves as much. Concurrently, the second differential control pulley 1313*d* rotates in the counterclockwise direction, and the first differential control pulley 1313*c* rotates in the clockwise direction. At the same time, the output unit 1313, which includes the output pulley 1313*a*, the extension portion 1313*b*, the first differential control pulley 1313*c*, and the second differential control pulley 1313*d*, rotates around the rotating axis of the output pulley 1313*a* in the direction opposite to the direction of the arrow R2 of FIG. 4A. Then, the rotation of the output unit 1313 is transmitted to the first jaw 121 of the end tool 120 through the operator control member 115, so that the first jaw 121 rotates in the direction of the arrow YJ of FIG. 2.

Also, when the actuation operator 113 rotates in the direction of the arrow A of FIG. 2, the second pulley 1131*b* of the actuation operator 113, the AC2 wire 135AC2 wound around the second pulley 1131*b*, the first pulley 1322*a* of the second input unit 1322 of the second differential pulley 132 around which the AC2 wire 135AC2 is wound, and the second pulley 1322*b* connected with the first pulley 1322*a* rotate together. However, the first input unit 1321 of the second differential pulley 132 that is connected with the yaw operator 112 does not rotate. In this manner, when the second input unit 1322 of the second differential pulley 132 rotates in the direction of an arrow R4 of FIG. 4B and the first input unit 1321 does not rotate, a portion wound around the second input unit 1322 of the differential control wire 135J21 rotates but a portion wound around the first input unit 1321 of the differential control wire 135J21 does not rotate. Accordingly, the wire wound around the first input unit 1321 is unwound as much as the rotation of the portion wound around the second input unit 1322 of the differential control wire 135J21, and the differential control wire 135J21 moves as much. Concurrently, the second differential control pulley 1323*d* rotates in the clockwise direction, and the first differential control pulley 1323*c* rotates in the counterclockwise direction. At the same time, the output unit 1323, which includes the output pulley 1323*a*, the extension portion 1323*b*, the first differential control pulley 1323*c*, and the second differential control pulley 1323*d*, rotates around the rotating axis of the output pulley 1323*a* in the direction of the arrow R4 of FIG. 4B. Then, the rotation of the output unit 1323 is transmitted to the second jaw 122 of the end tool 122 through the operator control member 115, so that the second jaw 122 rotates in the direction opposite to the direction of the arrow YJ of FIG. 2.

That is, when the first jaw 121 rotates in the direction of the arrow YJ of FIG. 2 and the second jaw 122 rotates in the direction opposite to the direction of the arrow YJ of FIG. 2, an actuation operation of the end tool 120 is performed.

There is a case where, in a differential pulley including two input units and one output unit, the rotation of one input unit does not generate the rotation of the output unit and generates the rotation of another input unit. In order to prevent this case, according to the present invention, in a situation where two operators are connected respectively to two differential pulleys, when one operator is connected with two input units of each of two differential pulleys, one of the wires connecting the operator and the input unit is twisted, thereby preventing a situation where the input of one operator causes another operator to rotate.

In order to describe this in more detail, a case where the second input unit 1312 of the first differential pulley 131 and the second input unit 1322 of the second differential pulley 132 also rotate in the same direction as a rotation input of the yaw operator 112 by the rotation input of the yaw operator 112 connected to the first input unit 1311 of the first differential pulley 131 and the first input unit 1321 of the second differential pulley 132 is assumed. In this case, the actuation operator 113 and the second input unit 1312 of the first differential pulley 131 are connected by the AC1 wire 135AC1 that is twisted one time, and the actuation operator 113 and the second input unit 1322 of the second differential pulley 132 are connected by the AC2 wire 135AC2 that is not twisted. Thus, rotations of the second input units 1312 and 1322 of the first and second differential pulleys 131 and 132 rotate the actuation operator 113 in opposite directions by the AC1 wire 135AC1 and the AC2 wire 135AC2. Therefore, the rotations offset each other and do not rotate the actuation operator 113, and the remaining rotation is transmitted to each of the output units 1313 and 1323 to rotate each of the output units 1313 and 1323.

This is also applied to the rotation input of the actuation operator 113. Thus, the rotation input of the actuation operator 113 does not cause the yaw operator 112 to rotate and is transmitted to each of the output units 1313 and 1323 to rotate each of the output units 1313 and 1323.

In summary, according to this configuration, the rotation input of one operator does not cause another operator to rotate and is transmitted to each output unit to rotate each output unit.

By this operational principle, even when the yaw operator 112 and the actuation operator 113 rotate simultaneously, the sum of (or the difference between) the rotation inputs of the yaw operator 112 and the actuation operator 113 is transmitted to the output units 1313 and 1323 of the first and second differential pulleys 131 and 132 through the first and second differential pulleys 131 and 132 to rotate the output units 1313 and 1323, and the rotations of the output units 1313 and 1323 are transmitted to the first and second jaws 121 and 122 of the end tool 120 through the operation control member 115, thus causing the first and second jaws 121 and 122 to rotate according to the operations of the yaw operator 112 and the actuation operator 113.

(End Tool)

Figure 5:
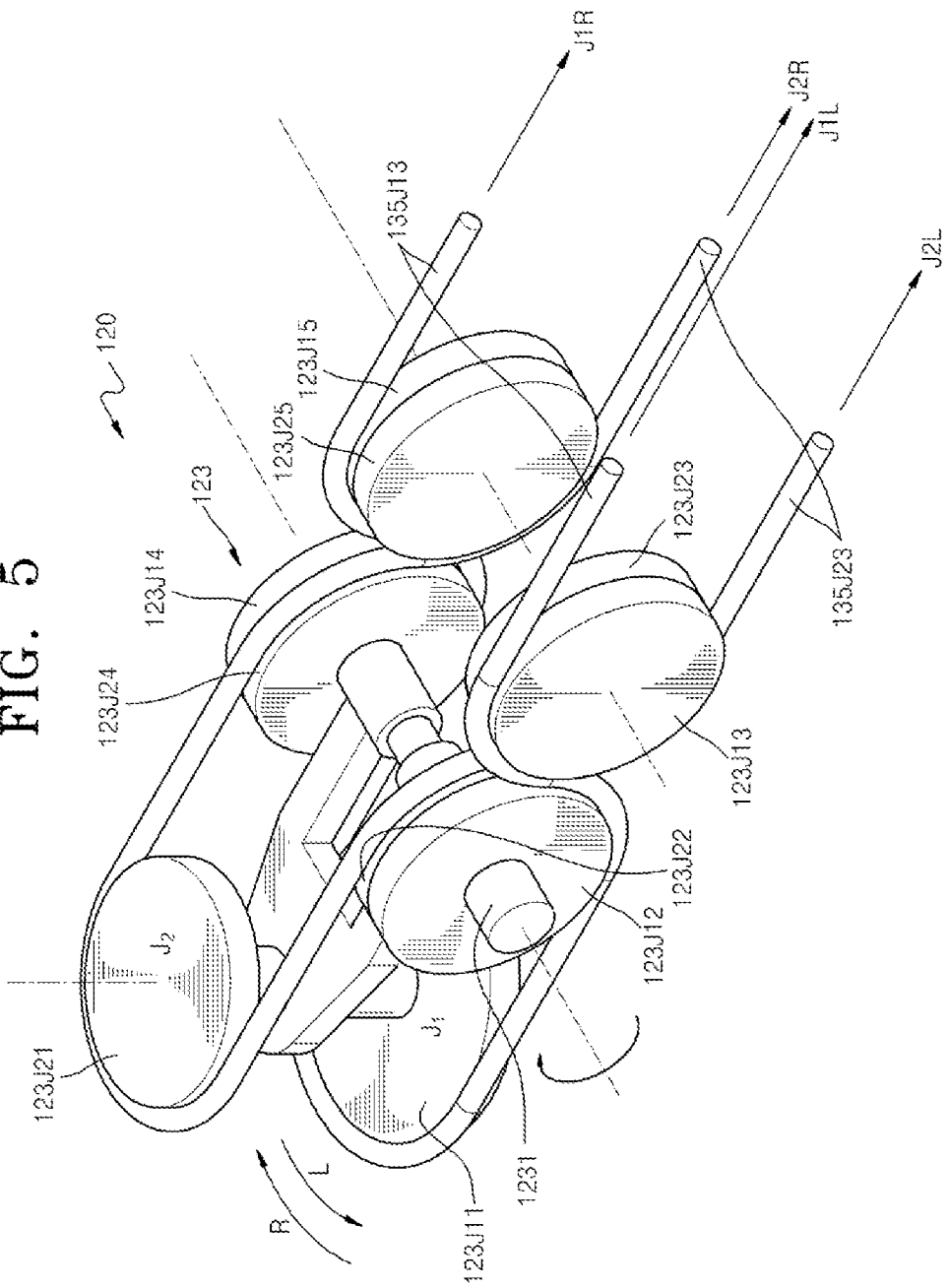
FIG. 5 is a detailed view of an end tool of the surgical instrument of FIG. 2.

FIG. 5 is a schematic view of the end tool 120 of the surgical instrument 100 of FIG. 2.

Referring to FIGS. 1, 2, and 5, the end tool 120 of the surgical instrument 100 according to the first embodiment of the present invention includes the end tool control member 123. The end tool control member 123 includes a J11 pulley 123J11, a J12 pulley 123J12, a J13 pulley 123J13, a J14 pulley 123J14, and a J15 pulley 123J15 that are related to the rotation motion of the first jaw 121, and a J21 pulley 123J21, a J22 pulley 123J22, a J23 pulley 123J23, a J24 pulley 123J24, and a J25 pulley 123J25 that are related to the rotation motion of the second jaw 122. Herein, the J12 pulley 123J12, the J14 pulley 123J14, the J22 pulley 123J22, and the J24 pulley 123J24 may be formed to rotate around an end tool pitch operating axis 1231. Although it is illustrated that pulleys facing each other are formed to be parallel to each other and have the same size, the present invention is not limited thereto, and the pulleys may be formed to have various positions and sizes suitable for the configuration of the end tool 120.

Herein, the end tool 120 of the surgical instrument 100 according to the first embodiment of the present invention includes the end tool control member 123 and only two wires, namely, a first jaw operating wire 135J13 and a second jaw operating wire 135J23, thereby making it possible to conveniently perform a pitch operation, a yaw operation, and an actuation operation of the end tool 120. This will be described below in more detail.

The J11 pulley 123J11 and the J21 pulley 123J21 are formed to face each other and rotate independently around the Z-axis direction. Although not illustrated in FIG. 5, the first jaw 121 may be coupled to the J11 pulley 123J11 to rotate along with the J11 pulley 123J11, and the second jaw 122 may be coupled to the J21 pulley 123J21 to rotate along with the J21 pulley 123J21. A yaw operation and an actuation operation of the end tool 120 are performed according to the rotations of the J11 pulley 123J11 and the J21 pulley 123J21. That is, the yaw operation is performed when the J11 pulley 123J11 and the J21 pulley 123J21 rotate in the same direction, and the actuation operation is performed when the J11 pulley 123J11 and the J21 pulley 123J21 rotate in opposite directions.

The elements related to the rotation of the J11 pulley 123J11 will be described below.

On one side of the J11 pulley 123J11, the J12 pulley 123J12 and the J14 pulley 123J14 are disposed to be spaced apart from each other by a predetermined distance and face each other. Herein, the J12 pulley 123J12 and the J14 pulley 123J14 are formed to rotate independently around the Y-axis direction. Also, on one side of the J12 pulley 123J12 and the J14 pulley 123J14, the J13 pulley 123J13 and the J15 pulley 123J15 are disposed to be spaced apart from each other by a predetermined distance and face each other. Herein, the J13 pulley 123J13 and the J15 pulley 123J15 are formed to rotate independently around the Y-axis direction. Although it is illustrated that all of the J12 pulley 123J12, the J13 pulley 123J13, the J14 pulley 123J14, and the J15 pulley 123J15 are formed to rotate around the Y-axis direction, the present invention is not limited thereto, and the rotating axes of the respective pulleys may be formed in various directions according to their configurations.

At least a portion of the first jaw operating wire 135J13 contacts the J13 pulley 123J13, the J12 pulley 123J12, the J11 pulley 123J11, the J14 pulley 123J14, and the J15 pulley 123J15, so that the first jaw operating wire 135J13 may move along the pulleys while rotating the pulleys.

Thus, when the first jaw operating wire 135J13 is pulled in the direction of an arrow J1R of FIG. 5, the first jaw operating wire 135J13 sequentially rotates the J15 pulley 123J15, the J14 pulley 123J14, the J11 pulley 123J11, the J12 pulley 123J12, and the J13 pulley 123J13. In this case, the J11 pulley 123J11 rotates in the direction of an arrow R of FIG. 5 to rotate the first jaw 121 together therewith.

On the other hand, when the first jaw operating wire 135J13 is pulled in the direction of an arrow J1L of FIG. 5, the first jaw operating wire 135J13 sequentially rotates the J13 pulley 123J13, the J12 pulley 123J12, the J11 pulley 123J11, the J14 pulley 123J14, and the J15 pulley 123J15. In this case, the J11 pulley 123J11 rotates in the direction of an arrow L of FIG. 5 to rotate the first jaw 121 together therewith.

The elements related to the rotation of the J21 pulley 123J21 will be described below.

On one side of the J21 pulley 123J21, the J22 pulley 123J22 and the J24 pulley 123J24 are disposed to be spaced apart from each other by a predetermined distance and face each other. Herein, the J22 pulley 123J22 and the J24 pulley 123J24 are formed to rotate independently around the Y-axis direction. Also, on one side of the J22 pulley 123J22 and the J24 pulley 123J24, the J23 pulley 123J23 and the J25 pulley 123J25 are disposed to be spaced apart from each other by a predetermined distance and face each other. Herein, the J23 pulley 123J23 and the J25 pulley 123J25 are formed to rotate independently around the Y-axis direction. Although it is illustrated that all of the J22 pulley 123J22, the J23 pulley 123J23, the J24 pulley 123J24, and the J25 pulley 123J25 are formed to rotate around the Y-axis direction, the present invention is not limited thereto, and the rotating axes of the respective pulleys may be formed in various directions according to their configurations.

At least a portion of the second jaw operating wire 135J23 contacts the J23 pulley 123J23, the J22 pulley 123J22, the J21 pulley 123J21, the J24 pulley 123J24, and the J25 pulley 123J25, so that the second jaw operating wire 135J23 may move along the pulleys while rotating the pulleys.

Thus, when the second jaw operating wire 135J23 is pulled in the direction of an arrow J2R of FIG. 5, the second jaw operating wire 135J23 sequentially rotates the J25 pulley 123J25, the J24 pulley 123J24, the J21 pulley 123J21, the J22 pulley 123J22, and the J23 pulley 123J23. In this case, the J21 pulley 123J21 rotates in the direction of the arrow R of FIG. 5 to rotate the second jaw 122 together therewith.

On the other hand, when the second jaw operating wire 135J23 is pulled in the direction of an arrow J2L of FIG. 5, the second jaw operating wire 135J23 sequentially rotates the J23 pulley 123J23, the J22 pulley 123J22, the J21 pulley 123J21, the J24 pulley 123J24, and the J25 pulley 123J25. In this case, the J21 pulley 123J21 rotates in the direction of the arrow L of FIG. 5 to rotate the second jaw 122 together therewith.

When one end portion of the first jaw operating wire 135J13 is pulled in the direction of the arrow J1R of FIG. 5 and the other end portion of the first jaw operating wire 135J13 is pulled in the direction of the arrow J1L of FIG. 5, the end tool control member 123 rotates around the end tool pitch operating axis 1231 in the counterclockwise direction, so that the end tool 120 rotates downward to perform a pitch motion.

On the other hand, when one end portion of the second jaw operating wire 135J23 is pulled in the direction of the arrow J2R of FIG. 5 and the other end portion of the second jaw operating wire 135J23 is pulled in the direction of the arrow J2L of FIG. 5, the end tool control member 123 rotates around the end tool pitch operating axis 1231 in the clockwise direction, so that the end tool 120 rotates upward to perform a pitch motion.

That is, since the end tool 120 includes the end tool control member 123 and only two wires, namely, the first jaw operating wire 135J13 and the second jaw operating wire 135J23, a pitch operation, a yaw operation, and an actuation operation of the end tool 120 may be conveniently performed. This will be described later in detail.

In the end tool control member 123 of the end tool 120 according to an embodiment of the present invention, the end tool pitch operating axis 1231 is disposed adjacent to the first and second jaws 121 and 122 (that is, the end tool pitch operating axis 1231 is disposed adjacent to the J12 pulley 123J12 and the J14 pulley 123J14, not to the J13 pulley 123J13 and the J15 pulley 123J15), thereby reducing a pitch rotation radius of the first and second jaws 121 and 122. Accordingly, a space necessary for a pitch operation of the first and second jaws 121 and 122 may be reduced.

Figure 5A:
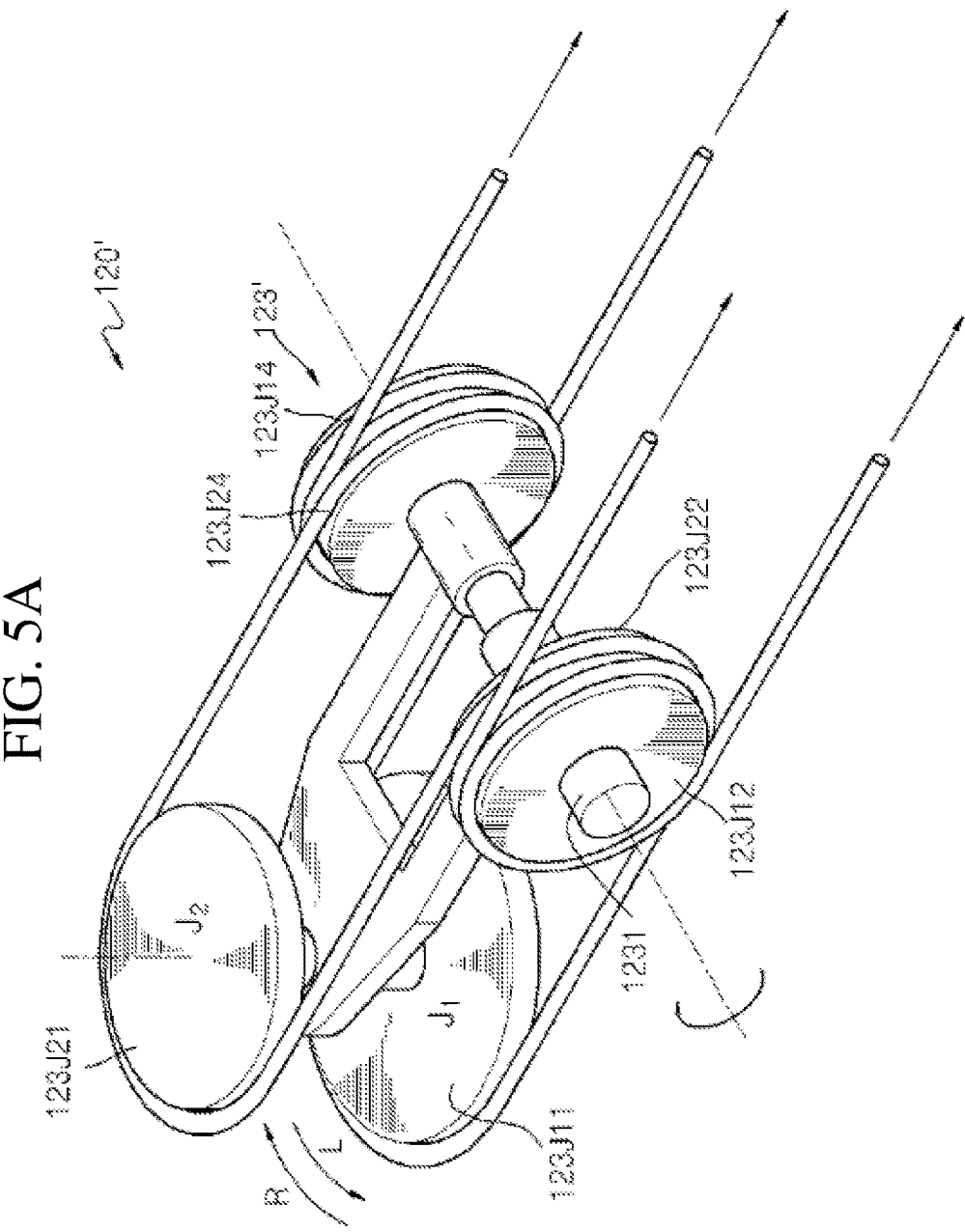
FIG. 5A illustrates a modification of the end tool of FIG. 5.

FIG. 5A illustrates a modification of the end tool 120 of FIG. 5.

Referring to FIG. 5A, an end tool 120' includes an end tool control member 123', and the end tool control member 123' includes a J11 pulley 123J11, a J12 pulley 123J12, a J14 pulley 123J14 related to the rotation motion of a first jaw, and a J21 pulley 123J21, a J22 pulley 123J22, a J24 pulley 123J24 related to the rotation motion of a second jaw. Herein, the J12 pulley 123J12, the J14 pulley 123J14, the J22 pulley 123J22, and the J24 pulley 123J24 may be formed to rotate around an end tool pitch operating axis 1231. Although it is illustrated that pulleys facing each other are formed to be parallel to each other and have the same size, the present invention is not limited thereto, and the pulleys may be formed to have various positions and sizes suitable for the configuration of the end tool 120.

In this modification, not two pairs of pulleys facing each other, but only a pair of pulleys (i.e., the J12 pulley 123J12 and the J14 pulley 123J14) are disposed on one side of the J11 pulley 123J11 coupled with the first jaw, wherein the first jaw operating wire 135J13 is wound one or more times around the pair of pulleys while contacting the pair of pulleys.

In detail, the J11 pulley 123J11 and the J21 pulley 123J21 are formed to face each other and rotate independently around the Z-axis direction.

On one side of the J11 pulley 123J11, the J12 pulley 123J12 and the J14 pulley 123J14 are disposed to be spaced apart from each other by a predetermined distance and face each other. Herein, the J12 pulley 123J12 and the J14 pulley 123J14 are formed to rotate independently around the Y-axis direction. At least a portion of the first jaw operating wire 135J13 contacts the J12 pulley 123J12, the J11 pulley 123J11, and the J14 pulley 123J14, so that the first jaw operating wire 135J13 may move along the pulleys while rotating the pulleys. Herein, the first jaw operating wire 135J13 may be wound one or more times around the J12 pulley 123J12 and then wound one or more times around the J14 pulley 123J14 through the J11 pulley 123J11.

Likewise, on one side of the J21 pulley 123J21, the J22 pulley 123J22 and the J24 pulley 123J24 are disposed to be spaced apart from each other by a predetermined distance and face each other. Herein, the J22 pulley 123J22 and the J24 pulley 123J24 are formed to rotate independently around the Y-axis direction. At least a portion of the second jaw operating wire 135J23 contacts the J22 pulley 123J22, the J21 pulley 123J21, and the J24 pulley 123J24, so that the second jaw operating wire 135J23 may move along the pulleys while rotating the pulleys. Herein, the second jaw operating wire 135J23 may be wound one or more times around the J22 pulley 123J22 and then wound one or more times around the J24 pulley 123J24 through the J21 pulley 123J21.

By the above configuration, the number of pulleys may be reduced, and thus the size of a surgical instrument may be further reduced.

(Pitch Operation Control and Wire Mirroring)

Figure 6:
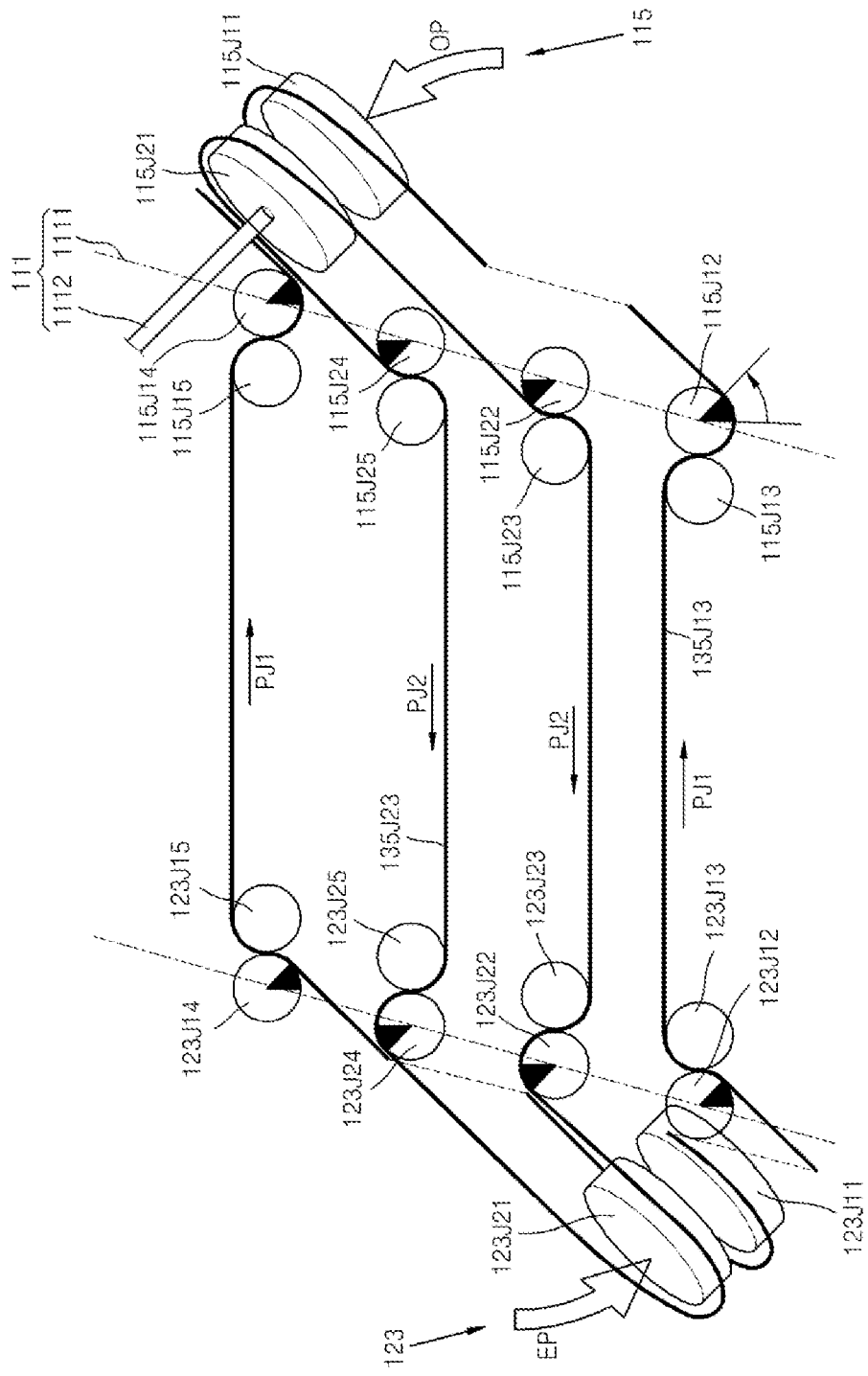
FIG. 6 is a schematic view illustrating a pitch operation of the surgical instrument of FIG. 2.

FIG. 6 is a schematic view illustrating a pitch operation of the surgical instrument 100 of FIG. 2.

As described above, the operator 110 of the surgical instrument 100 according to the first embodiment of the present invention further includes the operator control member 115 engaged with the pitch operating axis 1111 of the pitch operator 111. The operator control member 115 has substantially the same configuration of the end tool control member 123, and the end tool control member 123 and the operator control member 115 are disposed symmetrical to each other about the YZ plane of FIG. 1. In other words, it may be said that the end tool control member 123 and the operator control member 115 are mirrored with respect to the YZ plane of FIG. 1.

In detail, the operator control member 115 includes a J11 pulley 115J11, a J12 pulley 115J12, a J13 pulley 115J13, a J14 pulley 115J14, and a J15 pulley 115J15 that are related to the rotation motion of the first jaw 121, and a J21 pulley 115J21, a J22 pulley 115J22, a J23 pulley 115J23, a J24 pulley 115J24, and a J25 pulley 115J25 that are related to the rotation motion of the second jaw 122.

At least a portion of the first jaw operating wire 135J13 contacts the J13 pulley 115J13, the J12 pulley 115J12, the J11 pulley 115J11, the J14 pulley 115J14, and the J15 pulley 115J15, so that the first jaw operating wire 135J13 may move along the pulleys while rotating the pulleys.

At least a portion of the second jaw operating wire 135J23 contacts the J23 pulley 115J23, the J22 pulley 115J22, the J21 pulley 115J21, the J24 pulley 115J24, and the J25 pulley 115J25, so that the second jaw operating wire 135J23 may move along the pulleys while rotating the pulleys.

Herein, the rotating axis of the J12 pulley 115J12, the J14 pulley 115J14, the J22 pulley 115J22, and the J24 pulley 115J24 may be identical to the pitch operating axis 1111 of the pitch operator 111. Also, a bar extending from the rotating axis of the J11 pulley 115J11 and the J21 pulley 115J21 may be identical to the pitch operating bar 1112 of the pitch operator 111.

The pitch operation in the first embodiment of the present invention is performed as follows:

When the user grips the pitch operating bar 1112 of the pitch operator 111 of the operator 110 and rotates the pitch operating bar 1112 around the pitch operating axis 1111 in the direction of an arrow OP (Operator Pitch) of FIG. 6, the first jaw operating wire 135J13 is pulled toward the operator 110 and moves in the direction of an arrow PJ1 of FIG. 6. At the same time, the second jaw operating wire 135J23 is unwound from the operator 110, moves toward the end tool 120, and moves in the direction of an arrow PJ2 of FIG. 6. Then, as the first jaw operating wire 135J13 is pulled toward the operator 110, the J12 pulley 123J12 and the J14 pulley 123J14 rotate around the rotating axis (see FIG. 5) in the counterclockwise direction. At the same time, as the second jaw operating wire 135J23 is pulled toward the end tool 120, the J22 pulley 123J22 and the J24 pulley 123J24 rotate around the rotating axis (see FIG. 5) in the counterclockwise direction. Consequently, the end tool 120 rotates downward to perform a pitch motion.

In this manner, since the end tool control member 123 and the operator control member 115 are disposed symmetrical to each other (i.e., mirrored) with respect to the YZ plane of FIG. 1, the pitch operation may be conveniently performed. That is, the pitch operation may be performed regardless of the yaw operation and the actuation operation. Herein, the yaw operation refers to a rotating operation of the first and second jaws 121 and 122 according to the rotations of the J11 pulley 123J11 and the J21 pulley 123J21 of the end tool control member 123 and the J11 pulley 115J11 and the J21 pulley 115J21 of the operator control member 115.

(Overall Operation of First Embodiment)

Hereinafter, an overall configuration for the pitch operation, the yaw operation, and the actuation operation of the surgical instrument 100 according to the first embodiment of the present invention will be summarized with reference to the above descriptions.

For the configuration of the end tool 120 of the present embodiment, the operating force transmitter 130 capable of dividing the operation input of the operator 110 into a pitch operation, a yaw operation, and an actuation operation is necessary to perform the pitch, yaw, and actuation operations of the end tool 120. As described above, through the structure in which the end tool control member 123 and the operator control member 115 are disposed symmetrical to each other, the rotation operation of the pitch operator 111 enables the pitch operation of the end tool 120 regardless of the operations of the yaw operator 112 and the actuation operator 113. However, in order for the operations of the yaw operator 112 and the actuation operator 113 to lead to the yaw operation and the actuation operation of the end tool 120, the operations of the yaw operator 112 and the actuation operator 113 have to be converted into the operations of two jaws of the end tool 120. The rotation of the yaw operator 112 causes the two jaws to rotate in the same direction, and the rotation of the actuation operator 113 causes the two jaws to rotate in different directions. That is, the first jaw 121 rotates as much as the sum of the operation inputs of the yaw operator 112 and the actuation operator 113, and the second jaw 122 rotates as much as the difference between the operation inputs of the yaw operator 112 and the actuation operator 113. This may be expressed as the following equation:

$J1 = Y + A$ (the first jaw rotates in the same direction in both the yaw operation and the actuation operation.)

$J2 = Y - A$ (the second jaw rotates in the same direction in the yaw operation and rotates in an opposite direction in the actuation operation.)

(where Y denotes the rotation of the yaw operating pulley, and A denotes the rotation of the actuation operating pulley.)

To this end, the operating force transmitter includes a differential pulley that receives Y and A and outputs the sum (J1) of Y and A, and a differential pulley that receives Y and A and outputs the difference (J2) between Y and A, and the rotation of the output unit of each differential pulley is transmitted to each jaw of the end tool.

This will be described below in more detail.

First, the pitch operation will be described below.

As described above, when the user grips the pitch operating bar 1112 of the pitch operator 111 of the operator 110 and rotates the pitch operating bar 1112 around the pitch operating axis 1111 in the direction of the arrow OP of FIG. 6, the operator control member 115 also rotates around the pitch operating axis 1111. Then, the first jaw operating wire 135J13 wound around the operation control member 115 is pulled toward the operator 110 and moves in the direction of the arrow PJ1 of FIG. 6. At the same time, the second jaw operating wire 135J23 wound around the operation control member 115 is unwound from the operator control member 115 and moves in the direction of the arrow PJ2 of FIG. 6. Then, the end tool control member 123 connected with the first jaw operating wire 135J13 and the second jaw operating wire 135J23 rotates around the end tool pitch operating axis 1231 in the direction of an arrow EP of FIG. 6 to perform a pitch motion.

The yaw operation will be described below.

When the yaw operator 112 rotates in the direction of the arrow Y of FIG. 2, the first pulley 1121a of the yaw operator 112, the YC1 wire 135YC1 wound around the first pulley 1121a, and the first input unit 1311 of the first differential pulley 131, around which the YC1 wire 135YC1 is wound, rotate together. In this manner, when the first input unit 1311 of the first differential pulley 131 rotates, the rotating force of the differential control wire 135J11 connecting the first input unit 1311 and the output unit 1313 rotates the output unit 1313 in the direction of the arrow R1 of FIG. 4A. Then, the rotation of the output unit 1313 is transmitted to the operator control member 115 through the J12 wire 135J12 wound around the output unit 1313, to rotate the J11 pulley 115J11 (see FIG. 6) of the operator control member 115. Then, when the J11 pulley 115J11 of the operator control member 115 rotates, the first jaw operating wire 135J13 connected therewith is moved, and the first jaw 121 of the end tool 120 connected with the first jaw operating wire 135J13 rotates in the direction of the arrow YJ of FIG. 2.

Also, when the yaw operator 112 rotates in the direction of the arrow Y of FIG. 2, the second pulley 1121b of the yaw operator 112, the YC2 wire 135YC2 wound around the second pulley 1121b, and the first input unit 1321 of the second differential pulley 132, around which the YC2 wire 135YC2 is wound, rotate together therewith. In this manner, when the first input unit 1321 of the second differential pulley 132 rotates, the rotating force of the differential control wire 135J21 connecting the first input unit 1321 and the output unit 1323 rotates the output unit 1323 in the direction of the arrow R3 of FIG. 4B. Then, the rotation of the output unit 1323 is transmitted to the operator control member 115 through the J22 wire 135J22 wound around the output unit 1323, to rotate the J21 pulley 115J21 (see FIG. 6) of the operator control member 115. Then, when the J21 pulley 115J21 of the operator control member 115 rotates, the second jaw operating wire 135J23 connected therewith is moved, and the second jaw 122 of the end tool 120 connected with the second jaw operating wire 135J23 rotates in the direction of the arrow YJ of FIG. 2.

In this manner, when the yaw operator 112 is rotated in one direction, the first and second jaws 121 and 122 rotate in the same direction to perform a yaw operation. Herein, the surgical instrument 100 according to an embodiment of the present invention includes one or more differential pulleys, so that the operation of the yaw operator 112 is not accompanied by the operation of the actuation operator 113.

The actuation operation will be described below.

When the actuation operator 113 rotates in the direction of the arrow A of FIG. 2, the first pulley 1131a of the actuation operator 113, the AC1 wire 135AC1 wound around the first pulley 1131a, and the second input unit 1312 of the first differential pulley 131, around which the AC1 wire 135AC1 is wound, rotate together. Herein, since the AC1 wire 135AC1 is twisted one time, the rotating force of the actuation operator 113 is reversed and transmitted to the first differential pulley 131. In this manner, when the second input unit 1312 of the first differential pulley 131 rotates, the rotating force of the differential control wire 135J11 connecting the second input unit 1312 and the output unit 1313 rotates the output unit 1313 in a direction opposite to the direction of the arrow R2 of FIG. 4A. Then, the rotation of the output unit 1313 is transmitted to the operator control member 115 through the J12 wire 135J12 wound around the output unit 1313, to rotate the J11 pulley 115J11 (see FIG. 6) of the operator control member 115. Then, when the J11 pulley 115J11 of the operator control member 115 rotates, the first jaw operating wire 135J13 connected therewith is rotated, and the first jaw 121 of the end tool 120 connected with the first jaw operating wire 135J13 rotates in the direction of the arrow YJ of FIG. 2.

Also, when the actuation operator 113 rotates in the direction of the arrow A of FIG. 2, the second pulley 1131b of the actuation operator 113, the AC2 wire 135AC2 wound around the second pulley 1131b, and the second input unit 1322 of the second differential pulley 132, around which the AC2 wire 135AC2 is wound, rotate together. In this manner, when the second input unit 1322 of the second differential pulley 132 rotates, the rotating force of the differential control wire 135J21 connecting the second input unit 1322 and the output unit 1323 rotates the output unit 1323 in the direction of the arrow R4 of FIG. 4A. Then, the rotation of the output unit 1323 is transmitted to the operator control member 115 through the J22 wire 135J22 wound around the output unit 1323, to rotate the J21 pulley 115J21 (see FIG. 6) of the operator control member 115. Then, when the J21 pulley 115J21 of the operator control member 115 rotates, the second jaw operating wire 135J23 connected therewith is rotated, and the second jaw 122 of the end tool 120 connected with the second jaw operating wire 135J23 rotates in a direction opposite to the direction of the arrow YJ of FIG. 2.

In this manner, when the actuation operator 113 is rotated in one direction, the first and second jaws 121 and 122 rotate in opposite directions to perform an actuation operation.

Herein, the surgical instrument 100 according to an embodiment of the present invention includes one or more differential pulleys, so that the operation of the actuation operator 113 is not accompanied by the operation of the yaw operator 112.

Thus, according to the present invention, a surgical instrument performing an output operation of an end tool by the independent inputs of a pitch operator, a yaw operator, and an actuation operator may be implemented solely by a mechanical configuration without using motors, electronic control, or software. That is, since the pitch operation, the yaw operation, and the actuation operation, which affect each other, are separated from each other solely by a mechanism, the configuration of the surgical instrument may be significantly simplified.

Also, the rotating force of the operator 110 may be transmitted to the end tool 120 solely by a minimum wire and pulley structure. In particular, according to the present invention, since the operation direction of the operator 110 is intuitively identical to the operation direction of the end tool 120, the convenience of a surgical operator may be improved and the accuracy of a surgical operation may be improved. In addition, since the end tool 120 includes only two wires, namely, the first jaw operating wire 135J13 and the second jaw operating wire 135J23, the pitch operation, the yaw operation, and the actuation operation of the end tool 120 may be conveniently performed. Furthermore, since the end tool control member 123 and the operator control member 115 are disposed symmetrical to each other (i.e., mirrored) about the YZ plane of FIG. 1, the pitch operation may be conveniently performed. That is, the pitch operation may be performed regardless of the yaw operation and the actuation operation.

Mode of the Invention

<First Modification of Differential Pulley> (D1)

Figure 7:
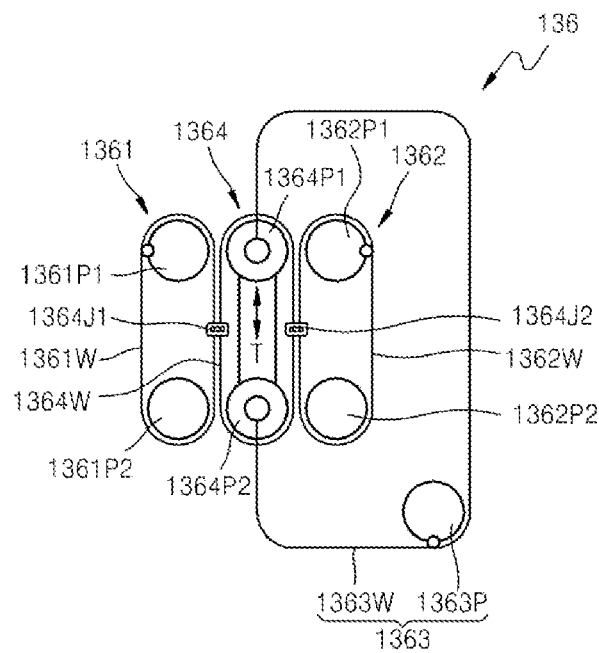
FIG. 7 is a view illustrating a first modification of the differential pulley of the surgical instrument illustrated in FIG. 2.
Figure 8:
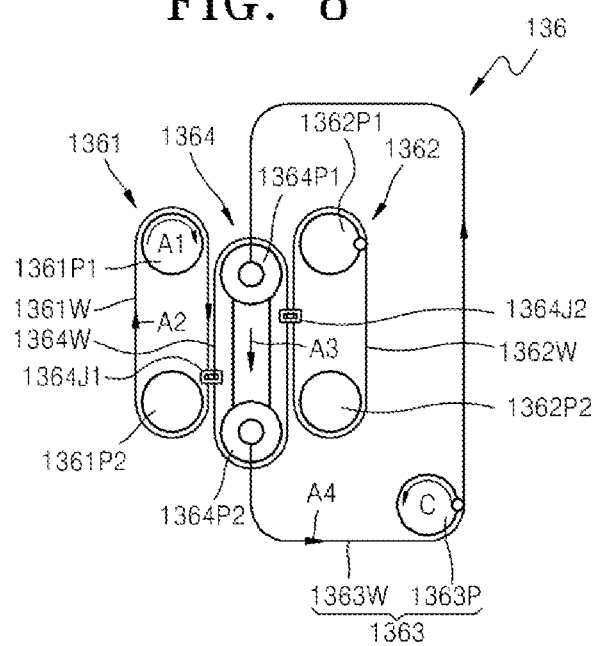
FIGS. 8 and 9 are views illustrating an operation of a first modification of the differential pulley illustrated in FIG. 7.
Figure 9:
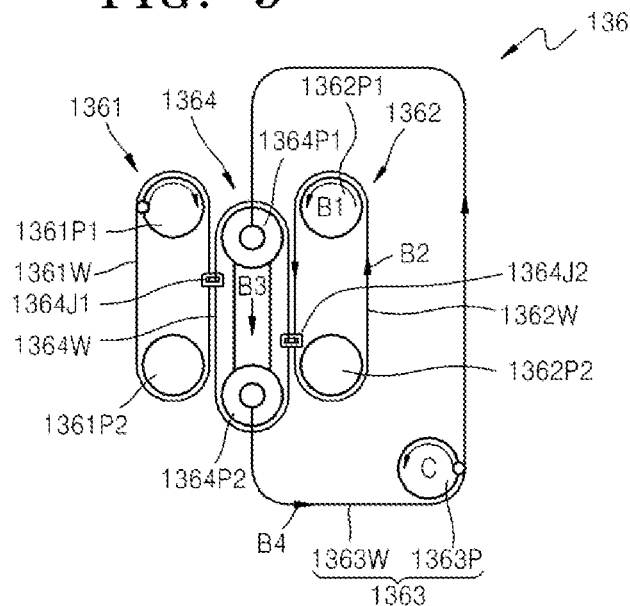

FIG. 7 is a view illustrating a first modification of the differential pulley of the surgical instrument 100 illustrated in FIG. 2, and FIGS. 8 and 9 are views illustrating an operation of the first modification of the differential pulley illustrated in FIG. 7.

As described above, the differential pulley according to the present invention includes two or more input units and one output unit, receives an input of rotating forces from the two or more input units, extracts a desired rotating force from the sum of (or the difference between) the input rotating forces, and outputs the desired rotating force through the output unit.

Referring to FIG. 7, the first modification of the differential pulley of the surgical instrument 100 includes a first input unit 1361, a second input unit 1362, an output unit 1363, and a differential control member 1364.

The first input unit 1361 includes a first pulley 1361P1, a second pulley 1361P2, and a first input wire 1361W. The first pulley 1361P1 and the second pulley 1361P2 are connected by the first input wire 1361W to rotate together.

The second input unit 1362 includes a first pulley 1362P1, a second pulley 1362P2, and a second input wire 1362W. The first pulley 1362P1 and the second pulley 1362P2 are connected by the second input wire 1362W to rotate together.

The output unit 1363 includes an output pulley 1363P and an output wire 1363W. The output pulley 1363P and the differential control member 1364 are connected by the output wire 1363W. When the differential control member 1364 translates, the output pulley 1363P connected with the differential control member 1364 by the output wire 1363W rotates.

The differential control member 1364 includes a first pulley 1364P1, a second pulley 1364P2, and a differential control wire 1364W. In addition, the differential control member 1364 includes a first differential joint 1364J1 and a second differential joint 1364J2. The first pulley 1364P1 and the second pulley 1364P2 are connected by the differential control wire 1364W to rotate together. The differential control member 1364 may translate in the direction of an arrow T of FIG. 7. For example, the differential control member 1364 may be installed on a guide rail (not illustrated) and may translate along the guide rail in the direction of the arrow T of FIG. 7.

The first differential joint 1364J1 may be coupled to the first input wire 1361W and the differential control wire 1364W to transmit a rotation of the first input wire 1361W to the differential control wire 1364W. The second differential joint 1364J2 may be coupled to the second input wire 1362W and the differential control wire 1364W to transmit a rotation of the second input wire 1362W to the differential control wire 1364W.

An operation of the first modification of the differential pulley will be described below.

First, a case where the first input unit 1361 rotates will be described below.

Referring to FIGS. 7 and 8, when the first pulley 1361P1 of the first input unit 1361 rotates in the direction of an arrow A1 of FIG. 8, the first input wire 1361W connected therewith moves along the first pulley 1361P1 in the direction of an arrow A2 of FIG. 8. Also, since the first input wire 1361W and the differential control wire 1364W are coupled to the first differential joint 1364J1, when the first input wire 1361W moves in the direction of the arrow A2 of FIG. 8, the first differential joint 1364J1 connected therewith also moves in the direction of the arrow A2. In this case, when the second input unit 1362 is fixed due to no rotation input, the second differential joint 1364J2 is also fixed. Thus, the differential control member 1364 translates in the direction of an arrow A3 as much as the movement of the first differential joint 1364J1, the first pulley 1364P1, the second pulley 1364P2, and the differential control wire 1364W also move together as much, and the first pulley 1364P1 and the second pulley 1364P2 rotate in the counterclockwise direction. When the differential control member 1364 moves in the direction of the arrow A3, the output wire 1363W connected therewith moves in the direction of an arrow A4 and thus the output pulley 1363P connected with the output wire 1363W rotates in the direction of an arrow C.

According to this configuration of the present invention, the rotation of the first input unit 1361 does not affect the second input unit 1362 and may be transmitted only to the output unit 1363 to rotate the output pulley 1363P.

A case where the second input unit 1372 rotates will be described below.

Referring to FIGS. 7 and 9, when the second pulley 1362P2 of the second input unit 1362 rotates in the direction of an arrow B1 of FIG. 9, the second input wire 1362W connected therewith moves along the first pulley 1362P1 in the direction of an arrow B2 of FIG. 9. Also, since the second input wire 1362W and the differential control wire 1364W are coupled to the second differential joint 1364J2, when the second input wire 1362W moves in the direction of the arrow B2 of FIG. 9, the second differential joint 1364J2 connected therewith also moves in the direction of the arrow B2. In this case, when the first input unit 1361 is fixed due to no rotation input, the first differential joint 1364J1 is also fixed. Thus, the differential control member 1364 translates in the direction of an arrow B3 as much as the movement of the second differential joint 1364J2, the first pulley 1364P1, the second pulley 1364P2, and the differential control wire 1364W also move together as much, and the first pulley 1364P1 and the second pulley 1364P2 rotate in the clockwise direction. When the differential control member 1364 moves in the direction of the arrow B3, the output wire 1363W connected therewith moves in the direction of an arrow B4 and thus the output pulley 1363P connected with the output wire 1363W rotates in the direction of the arrow C.

According to this configuration of the present invention, the rotation of the second input unit 1362 does not affect the first input unit 1361 and may be transmitted only to the output unit 1363 to rotate the output pulley 1363P.

A case where the first input unit 1371 and the second input unit 1372 rotate together will be described below.

When the first pulley 1361P1 of the first input unit 1361 rotates in the clockwise direction, the output pulley 1363P of the output unit 1363 rotates in the counterclockwise direction; and when the first pulley 1362P1 of the second input unit 1362 rotates in the counterclockwise direction, the output pulley 1363P of the output unit 1363 rotates in the counterclockwise direction. Thus, when the first pulley 1361P1 of the first input unit 1361 and the second pulley 1362P1 of the second input unit 1362 rotate in opposite directions, the output pulley 1363P of the output unit 1363 rotates as much as the sum of the two rotating forces. On the other hand, when the first pulley 1361P1 of the first input unit 1361 and the second pulley 1362P1 of the second input unit 1362 rotate in the same direction, the output pulley 1363P of the output unit 1363 rotates as much as the difference between the two rotating forces.

Thus, according to the present invention, when only one of the two or more input units rotates, only the output unit may be rotated without rotating other input units. Also, when the two or more input units rotate together, a single rotating force equal to the sum of (or the difference between) the rotating forces of the two input units may be output through the output unit.

The differential pulley of the third modification is a modification of the differential pulley illustrated in FIGS. 4A and 4B, and an example of applying the differential pulley of the third modification to the surgical instrument will not be described herein.

<Second Modification of Differential Pulley> (D2)

Figure 10:
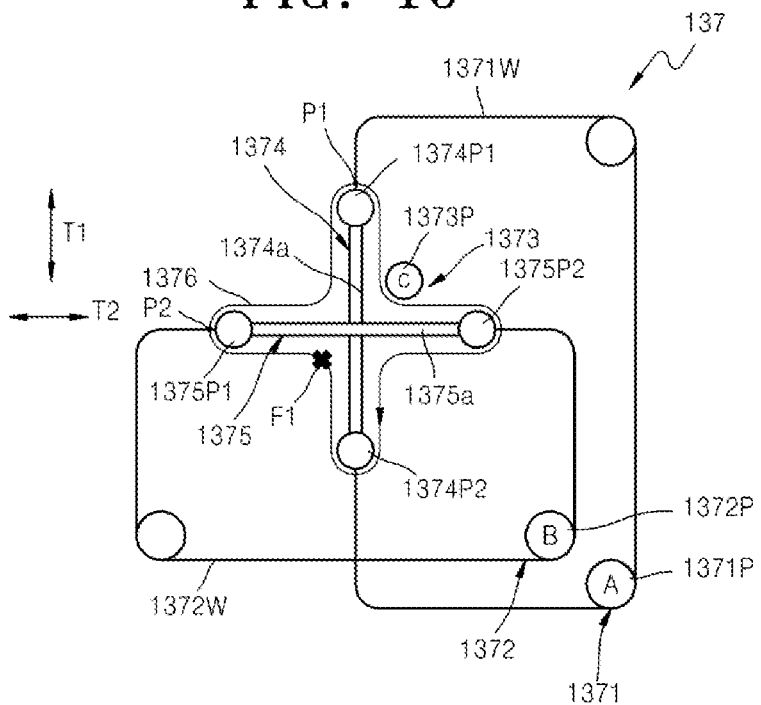
FIG. 10 is a view illustrating a second modification of the differential pulley of the surgical instrument illustrated in FIG. 2.
Figure 11:
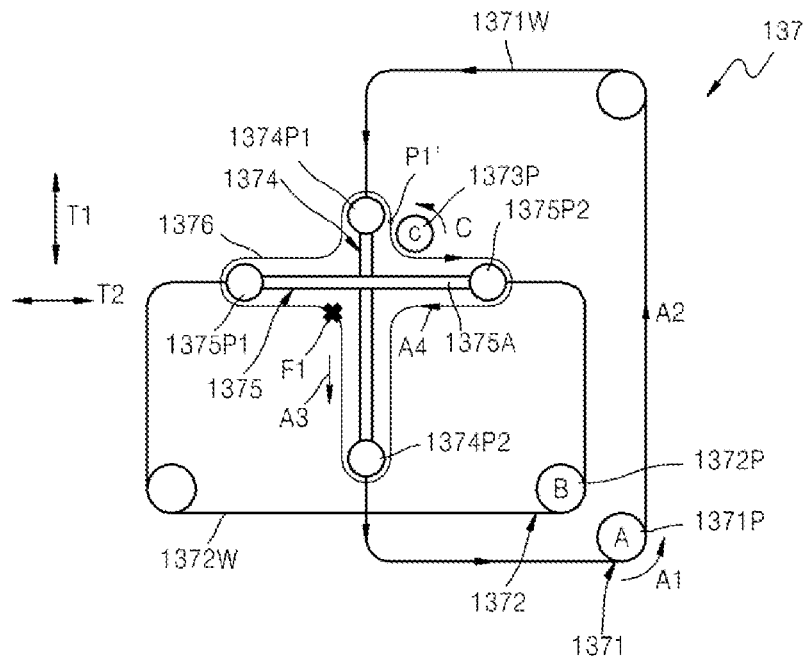
FIGS. 11 and 12 are views illustrating an operation of the second modification of the differential pulley illustrated in FIG. 10.
Figure 12:
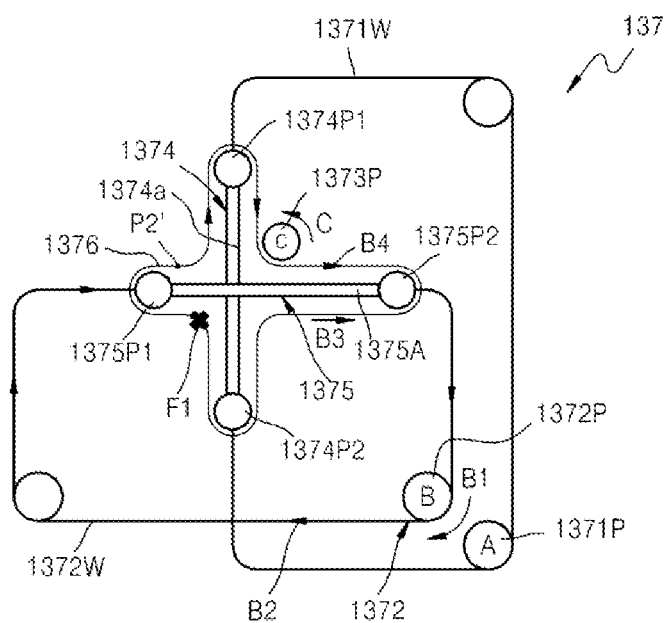
Figure 13A:
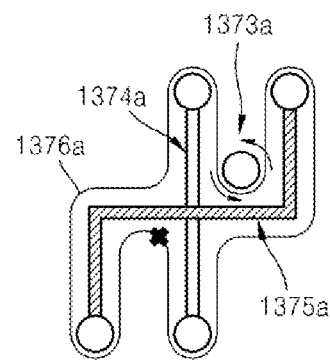
FIGS. 13A to 13E are views illustrating other examples of the second modification of the differential pulley illustrated in FIG. 10.
Figure 13B:
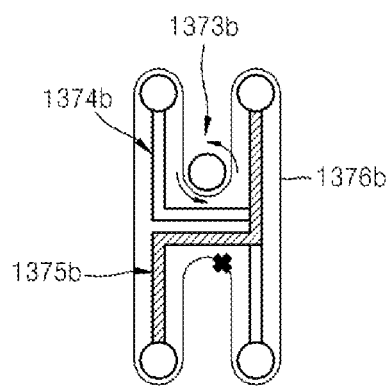
Figure 13C:
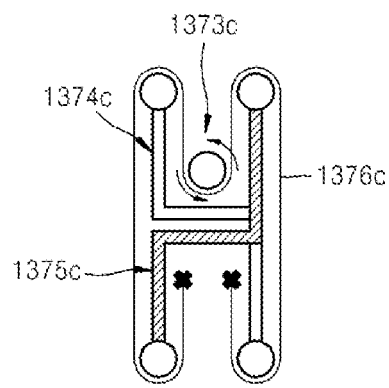
Figure 13D:
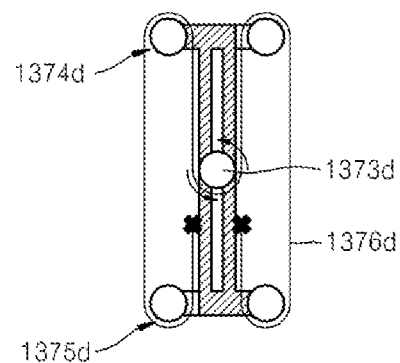
Figure 13E:
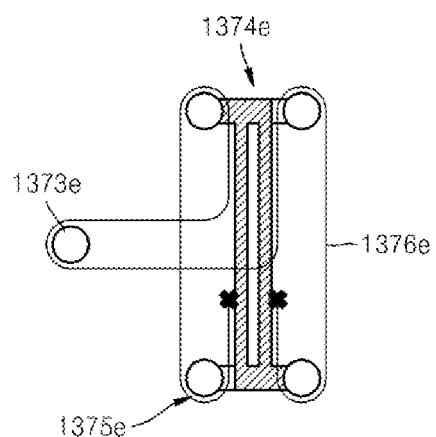

FIG. 10 is a view illustrating a second modification of the differential pulley of the surgical instrument 100 illustrated in FIG. 2, and FIGS. 11 and 12 are views illustrating an operation of the second modification of the differential pulley illustrated in FIG. 10.

As described above, the differential pulley according to the present invention includes two or more input units and one output unit, and outputs rotating forces, which are input from the two or more input units, as a desired rotating force, while each of the two or more input units does not affect other input units.

Referring to FIG. 10, the second modification of the differential pulley of the surgical instrument includes a first input unit 1371, a second input unit 1372, an output unit 1373, a first differential control member 1374, a second differential control member 1375, and a differential control wire 1376.

The first input unit 1371 includes a first input pulley 1371P and a first input wire 1371W. The first input pulley 1371P is connected with the first input wire 1371W to rotate along with the first input wire 1371W.

The second input unit 1372 includes a second input pulley 1372P and a second input wire 1372W. The second input pulley 1372P is connected with the second input wire 1372W to rotate along with the second input wire 1372W.

The output unit 1373 includes an output pulley 1373P. The output pulley 1373P is connected with the differential control wire 1376 to rotate along with the differential control wire 1376.

The first differential control member 1374 includes a first pulley 1374P1, a second pulley 1374P2, and a first differential control bar 1374a. The first pulley 1374P1 and the second pulley 1374P2 are respectively formed at both end portions of the first differential control bar 1374a and may rotate independently. Also, both end portions of the first input wire 1371W are coupled to both end portions of the first differential control member 1374. The first differential control member 1374 may translate in the direction of an arrow T1 of FIG. 10. For example, the first differential control member 1374 may be installed on a guide rail (not illustrated), and may translate along the guide rail in the direction of the arrow T1 of FIG. 10. Thus, when the first input pulley 1371P rotates, the first input wire 1371W connected therewith rotates, and when the first input wire 1371W rotates, the first differential control member 1374 coupled to both end portions thereof translates in the direction of the arrow T1 of FIG. 10.

The second differential control member 1375 includes a first pulley 1375P1, a second pulley 1375P2, and a second differential control bar 1375a. The first pulley 1375P1 and the second pulley 1375P2 are respectively formed at both end portions of the second differential control bar 1375a and may rotate independently. Also, both end portions of the second input wire 1372W are coupled to both end portions of the second differential control member 1375, respectively. The second differential control member 1375 may translate in the direction of an arrow T2 of FIG. 10. For example, the second differential control member 1375 may be installed on a guide rail (not illustrated), and may translate along the guide rail in the direction of the arrow T2 of FIG. 10. Thus, when the second input pulley 1372P rotates, the second input wire 1372W connected therewith rotates, and when the second input wire 1372W rotates, the second differential control member 1375 coupled to both end portions thereof translates in the direction of the arrow T2 of FIG. 10.

The differential control wire 1376 is connected along the first pulley 1374P1 of the first differential control member 1374, the first pulley 1375P1 of the second differential control member 1375, the second pulley 1374P2 of the first differential control member 1374, and the second pulley 1375P2 of the second differential control member 1375. The differential control wire 1376 is wound along the four pulleys, and is formed to move according to the translation motions of the first differential control member 1374 and the second differential control member 1375. Herein, a fixed point F1 may be formed at the differential control wire 1376, as a reference point for the movement of the differential control wire 1376.

An operation of the second modification of the differential pulley will be described below.

First, a case where the first input unit 1371 rotates will be described below.

Referring to FIGS. 10 and 11, when the first input pulley 1371P1 of the first input unit 1371 rotates in the direction of an arrow A1 of FIG. 11, the first input wire 1371W connected therewith moves along the first input pulley 1371P1 in the direction of an arrow A2 of FIG. 11. Since the first input wire 1371W is connected with the first differential control member 1374, when the first input wire 1371W moves in the direction of the arrow A2 of FIG. 11, the first differential control member 1374 translates in the direction of an arrow A3. When the first differential control member 1374 translates in the direction of the arrow A3, a point P1 of the differential control wire 1376 of FIG. 10 moves to a point P1' of the differential control wire 1376 of FIG. 11, and thus the differential control wire 1376 moves in the direction of an arrow A4 of FIG. 11. Thus, the output pulley 1373P connected with the differential control wire 1376 rotates in the direction of an arrow C. In this case, the first pulley 1374P1 and the second pulley 1374P2 of the first differential control member 1374 and the second pulley 1375P2 of the second differential control member 1375 rotate in the clockwise direction.

According to this configuration of the present invention, the rotation of the first input unit 1371 does not affect the second input unit 1372 and may be transmitted only to the output unit 1373 to rotate the output pulley 1373P.

A case where the second input unit 1372 rotates will be described below.

Referring to FIGS. 10 and 12, when the second input pulley 1372P of the second input unit 1372 rotates in the direction of an arrow B1 of FIG. 12, the second input wire 1372W connected therewith moves along the second input pulley 1372P in the direction of an arrow B2 of FIG. 12. Since the second input wire 1372W is connected with the second differential control member 1375, when the second input wire 1372W moves in the direction of the arrow B2 of FIG. 12, the second differential control member 1375 translates in the direction of an arrow B3. When the second differential control member 1375 translates in the direction of the arrow B3, a point P2 of the differential control wire 1376 of FIG. 10 moves to a point P2' of the differential control wire 1376 of FIG. 12, and thus the differential control wire 1376 moves in the direction of an arrow B4 of FIG. 12. Thus, the output pulley 1373P connected with the differential control wire 1376 rotates in the direction of an arrow C. In this case, the first pulley 1375P1 and the second pulley 1375P2 of the second differential control member 1375 and the first pulley 1374P1 of the first differential control member 1374 rotate in the clockwise direction.

According to this configuration of the present invention, the rotation of the second input unit 1372 does not affect the first input unit 1371 and may be transmitted only to the output unit 1373 to rotate the output pulley 1373P.

A case where the first input unit 1371 and the second input unit 1372 rotates together will be described below.

When the first input pulley 1371P of the first input unit 1371 rotates in the counterclockwise direction, the output pulley 1373P of the output unit 1373 rotates in the counterclockwise direction; and when the second input pulley 1372P of the second input unit 1372 rotates in the clockwise direction, the output pulley 1373P of the output unit 1373 rotates in the counterclockwise direction. Thus, when the first input pulley 1371P of the first input unit 1371 and the second input pulley 1372P of the second input unit 1372 rotate in opposite directions, the output pulley 1373P of the output unit 1373 rotates as much as the sum of the two rotating forces. On the other hand, when the first input pulley 1371P of the first input unit 1371 and the second input pulley 1372P of the second input unit 1372 rotate in the same direction, the output pulley 1373P of the output unit 1373 rotates as much as the difference between the two rotating forces.

Thus, according to the present invention, when only one of the two or more input units rotates, only the output unit may be rotated without rotating other input units. Also, when the two or more input units rotate together, a single rotating force equal to the sum of (or the difference between) the rotating forces of the two input units may be output through the output unit.

Other examples of the second modification of the differential pulley of the surgical instrument will be described below. FIGS. 13A to 13E are views illustrating other examples of the second modification of the differential pulley illustrated in FIG. 18. In FIGS. 13A to 13E, the first input and the second input are omitted, and first differential control members 1374*a* to 1374*e*, second differential control members 1375*a* to 1375*e*, output units 1373*a* to 1373*e*, and differential control wires 1376*a* to 1376*e* connecting them are illustrated. Although their external shapes are slightly different from each other, the respective examples are substantially identical to the second modification of the differential pulley of FIGS. 10 to 12 in that when the first input unit (not illustrated) rotates, the first differential control members 1374*a* to 1374*e* translate vertically to rotate the differential control wires 1376*a* to 1376*e* to rotate the output units 1373*a* to 1373*e*, and when the second input unit (not illustrated) rotates, the second differential control members 1375*a* to 1375*e* translate vertically to rotate the differential control wires 1376*a* to 1376*e* to rotate the output units 1373*a* to 1373*e*.

The differential pulley of the third modification is a modification of the differential pulley illustrated in FIGS. 4A and 4B, and an example of applying the differential pulley of the third modification to the surgical instrument will not be described herein.

<Third Modification of Differential Pulley> (D4)

Figure 14:
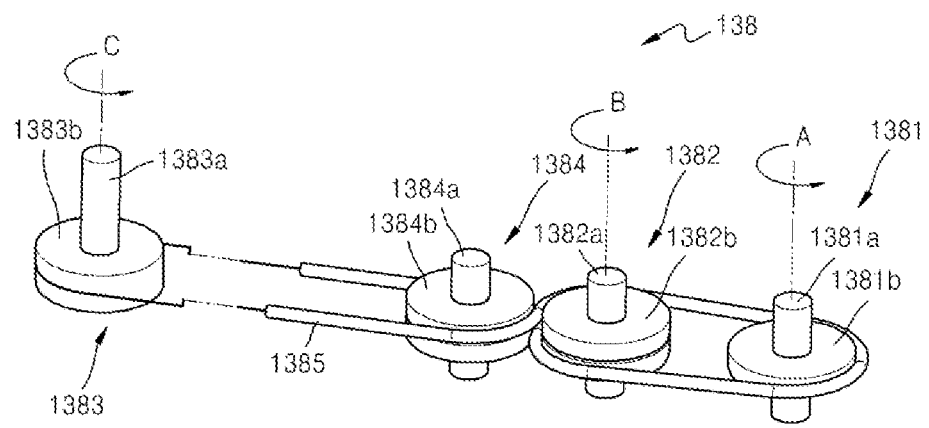
FIGS. 14 and 15 are views illustrating a third modification of the differential pulley of the surgical instrument illustrated in FIG. 2.
Figure 15:
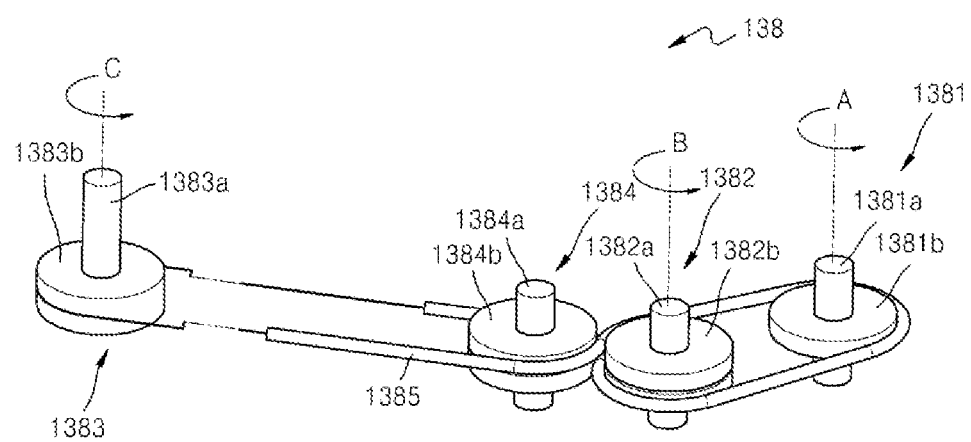

FIGS. 14 and 15 are views illustrating a third modification of the differential pulley of the surgical instrument 100 illustrated in FIG. 2.

As described above, the differential pulley according to the present invention includes two or more input units and one output unit, and outputs rotating forces, which are input from the two or more input units, as a desired rotating force, while each of the two or more input units does not affect other input units.

Referring to FIGS. 14 and 15, the third modification of the differential pulley of the surgical instrument includes a first input unit 1381, a second input unit 1382, an output unit 1383, and a connector 1384.

The first input unit 1381 includes a first rotating axis 1381*a* and a first input pulley 1381*b*, and the first input pulley 1381*b* is coupled with the first rotating axis 1381*a* to rotate around the first rotating axis 1381*a*.

The second input unit 1382 includes a second rotating axis 1382*a* and two second input pulleys 1382*b* facing each other, and the two second input pulleys 1382*b* are not coupled with the second rotating axis 1382*a* and rotate around the second rotating axis 1382*a*. The first input unit 1381 is formed to extend from the second input pulley 1382*b*. That is, since the first input pulley 1381*b* is connected to the second input pulley 1382*b* by a connecting member (not illustrated), when the second input pulley 1382*b* rotates, the first input unit 1381, including the first input pulley 1381*b* connected therewith, rotates.

The output unit 1383 includes a third rotating axis 1383*a* and an output pulley 1383*b*, and the output pulley 1383*b* is coupled with the third rotating axis 1383*a* to rotate around the third rotating axis 1383*a*.

The connector 1384 includes a fourth rotating axis 1384*a* and two connecting pulleys 1384*b* facing each other, and the two connecting pulleys 1384*b* are not coupled with the fourth rotating axis 1384*a* and rotate around the fourth rotating axis 1384*a*.

A differential control wire 1385 is formed to sequentially contact the output unit 1383, one of the two connecting pulleys 1384*b*, one of the two input pulleys 1382*b*, the first input pulley 1381*b*, the other of the two second input pulleys 1382*b*, the other of the two connecting pulleys 1384*b*, and the output unit 1383 and rotate along the output unit 1383, the connector 1384, the second input unit 1382, and the first input unit 1381.

Although not illustrated, a coupling member (not illustrated) connecting the first input unit 1381 and the second input unit 1382 may be further provided. The first rotating axis 1381*a* of the first input unit 1381 and the second rotating axis 1382*a* of the second input unit 1382 may be connected to the coupling member. Since the coupling member and the second rotating axis 1382*a* are fixedly coupled, when the second rotating axis 1382*a* rotates, the coupling member and the first input unit 1381 connected therewith rotate together therewith. On the other hand, since the coupling member and the first rotating axis 1381*a* are not fixedly coupled, even when the first rotating axis 1381*a* rotates, the coupling member may not rotate.

An operation of the third modification of the differential pulley will be described below.

First, a case where the first input unit 1381 rotates will be described below. When the first input pulley 1381*b* of the first input unit 1381 rotates around the first rotating axis 1381*a*, the differential control wire 1385 and the first input pulley 1381*b* rotate together by a frictional force or a fixed point and thus the differential control wire 1385 wound around the two second input pulleys 1382*b* and the connecting pulley 1384*b* also move. Consequently, the output pulley 1383*b* of the output unit 1383 connected to the opposite side of the differential control wire 1385 also rotate around the third rotating axis 1383*a*. In this case, the two second input pulleys 1382*a* and the two connecting pulleys 1384*b*, around which the moving differential control wire 1385 is wound, also rotate together.

A case where the second input unit 1382 rotates will be described below. When the second input pulley 1382*b* of the second input unit 1382 rotates around the second rotating axis 1382*a* in the state of FIG. 14, the first input unit 1381 rotates around the second rotating axis 1382*a* in the counterclockwise direction as illustrated in FIG. 15. In this case, when there is no rotation input to the first input unit 1381 and thus the rotation of the differential control wire 1385 wound around the first input pulley 1381*b* is relatively small on the first rotating axis 1381*a*, the differential control wire 1385 wound around the first rotating axis 1381*a* rotates around the second rotating axis 1382*a*. Accordingly, the differential control wire 1385 wound around the two second input pulleys 1382*b* is pulled and extended to rotate the two second input pulleys 1382*b*. The movement of the differential control wire 1385 on the two second input pulleys 1382*b* causes the two connecting pulleys 1384*b* and the output pulley 1383*b* to rotate.

Thus, according to the present invention, the rotation of one of the two or more input units may lead to the rotation of the output unit without rotating other input units. Also, when the two or more input units rotate together, a single rotating force equal to the sum of (or the difference between) the rotating forces of the two input units may be output through the output unit.

The third modification of the differential pulley is different from the first and second modifications of the differential pulley in that one input unit is provided on the rotating axis of another input unit and the position of the input unit rotates according to another rotation input. That is, while the input units are disposed independently of each other in the first and second modifications of the differential pulley, one input unit is disposed on a coordinate system of another input unit in the third modification of the differential pulley. As an example of this, in a second embodiment, one operation input unit is provided on another operation input unit, and the operation input unit also rotates or moves together when the other operation input unit rotates or moves.

Although it is illustrated that the output unit 1383, the connector 1384, the second input unit 1382, and the first input unit 1381 are sequentially arranged in the order stated, the present invention is not limited thereto. For example, the positions of the connector 1384 and the second input unit 1382 may be interchanged with each other. Also in this case, the first input pulley may be connected to the second input pulley by a connecting member (not illustrated), and when the second input pulley rotates, the first input pulley of the first input unit and the connecting pulley of the connector connected thereto may rotate together therewith.

The differential pulley of the third modification is a modification of the differential pulley illustrated in FIGS. 4A and 4B, and an example of applying the differential pulley of the third modification to the surgical instrument will not be described herein.

<Differential Gear>

Figure 16:
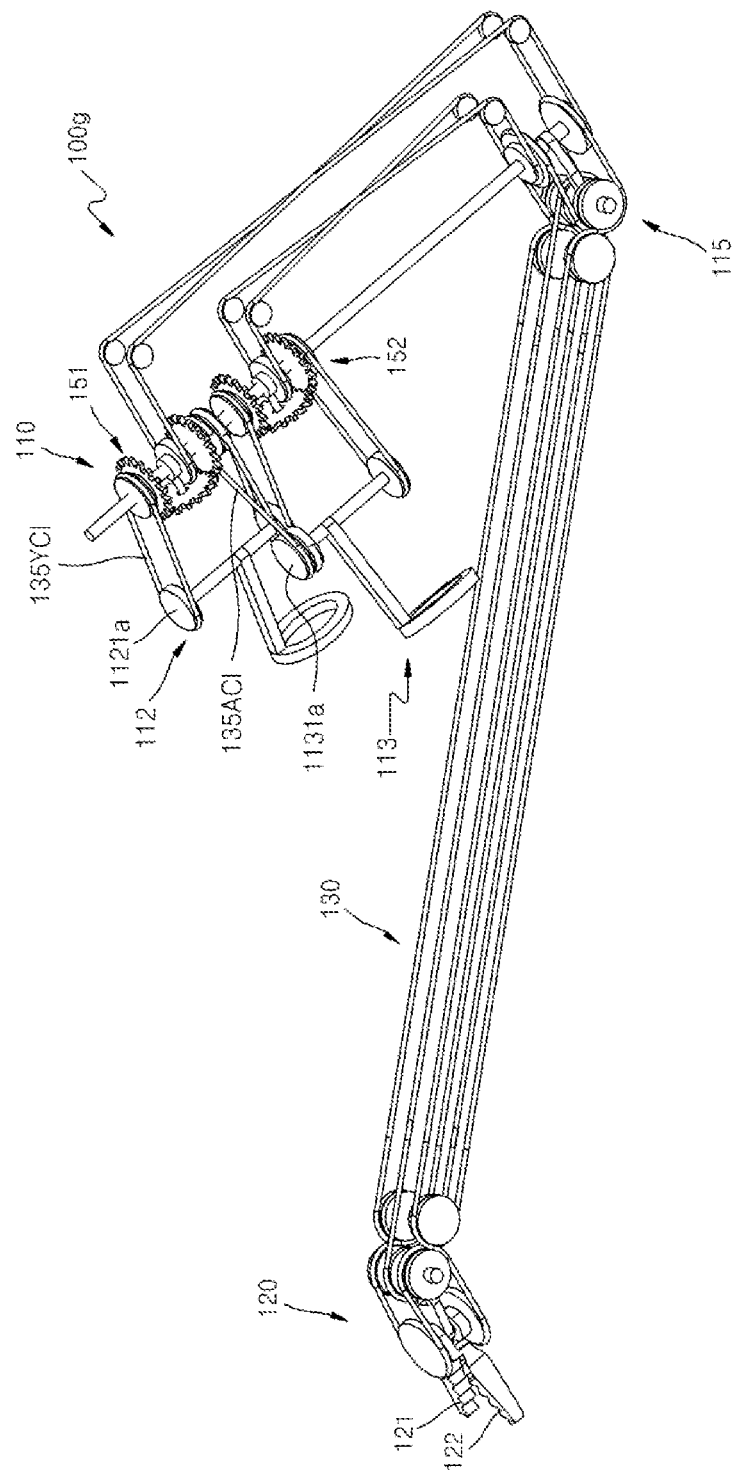
FIG. 16 is a view illustrating a surgical instrument according to a modification of an operating force transmitter of the surgical instrument illustrated in FIG. 2.
Figure 17:
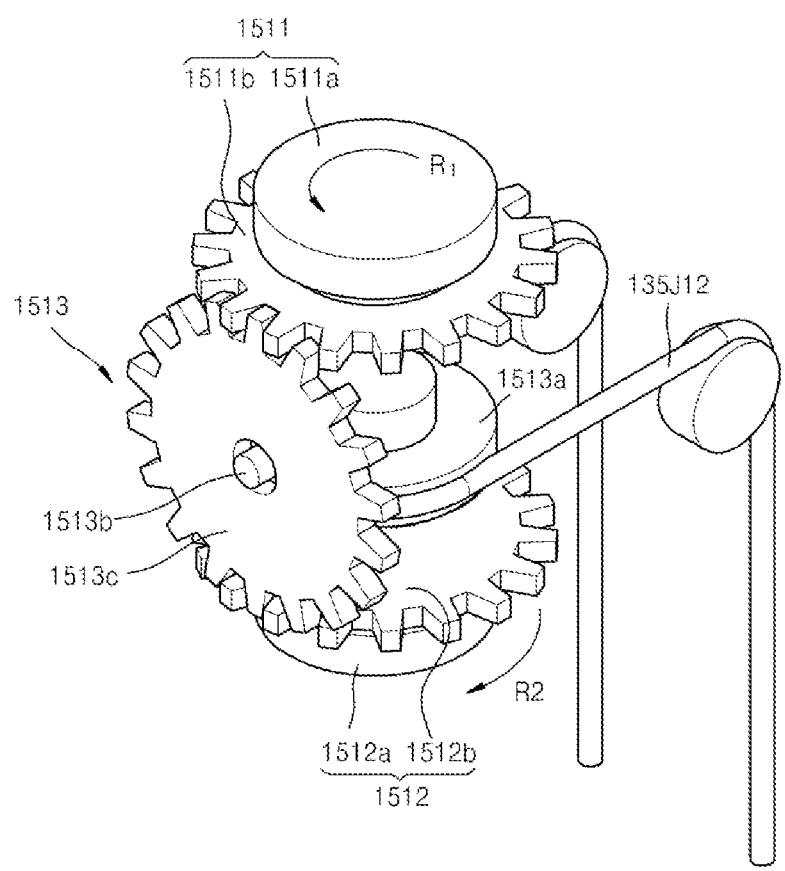
FIG. 17 is a detailed view of a differential gear of FIG. 16.

FIG. 16 is a view illustrating a surgical instrument 100g according to a modification of the operating force transmitter 130 of the surgical instrument 100 illustrated in FIG. 2, and FIG. 17 is a detailed view of a differential gear of FIG. 16. Since the surgical instrument 100g according to a modification of the operating force transmitter 130 of the first embodiment of the present invention is similar to the surgical instrument 100 according to the first embodiment of the present invention and is different from the surgical instrument 100 in terms of the configuration of the operating force transmitter 130, the configuration of the operating force transmitter 130 will be mainly described below.

In this modification, a differential gear is used instead of the differential pulleys of FIGS. 2 and 4A. That is, the differential gear of the surgical instrument 100g illustrated in FIGS. 16 and 17 may be considered as a structure in which the pulley and wire of the differential pulley of the surgical instrument 100 illustrated in FIG. 4A are replaced with a gear.

Referring to FIGS. 16 and 17, the surgical instrument 100g according to a modification of the operating force transmitter 130 of the first embodiment of the present invention includes an operator 110, an end tool 120, an operating force transmitter 130, and a connector (not illustrated). The operating force transmitter 130 includes a first differential gear 151 and a second differential gear 152.

In detail, the first differential gear 151 includes a first input unit 1511, a second input unit 1512, and an output unit 1513.

The first input unit 1511 includes a first pulley 1511a and a first gear 1511b. The first pulley 1511a and the first gear 1511b rotate together around the same rotating axis. Herein, the first pulley 1511a of the first input unit 1511 is connected with the first pulley 1121a of the yaw operator 112 by the YC1 wire 135YC1 to transmit a rotation of the yaw operator 112 to the first input unit 1511. Also, the first gear 1511b of the first input unit 1511 is connected with the output unit 1513 to transmit a rotation of the first input unit 1511 to the output unit 1513.

The second input unit 1512 includes a second pulley 1512a and a second gear 1512b. The second pulley 1512a and the second gear 1512b rotate together around the same rotating axis. Herein, the second pulley 1512a of the second input unit 1512 is connected with the first pulley 1131a of the actuation operator 113 by the AC1 wire 135AC1 to transmit a rotation of the actuation operator 113 to the second input unit 1512. Also, the second gear 1512b of the second input unit 1512 is connected with the output unit 1513 to transmit a rotation of the second input unit 1512 to the output unit 1513.

The output unit 1513 includes an output pulley 1513a, an extension portion 1513b, and a differential control gear 1513c. Herein, the output pulley 1513a of the output unit 1513 is connected with the operator control member 115 by the J12 wire 135J12 to transmit a rotation of the output unit 1513 to the first jaw 121 of the end tool 120 through the operator control member 115. The extension portion 1513b extends in one direction from a rotating axis of the output pulley 1513a to rotate around the rotating axis of the output pulley 1513a along with the output pulley 1513a. The extension portion 1513b is inserted through the differential control gear 1513c such that the differential control gear 1513c rotates around the extension portion 1513b.

Herein, the first input unit 1511, the second input unit 1512, and the output unit 1513 rotate independently around independent axes.

Herein, the first differential gear 151 includes the first input unit 1511, the second input unit 1512, and the output unit 1513, receives an input of rotating forces from the first input unit 1511 and the second input unit 1512, and outputs the sum of (or the difference between) the rotating forces through the output unit 1513. That is, when only the first input unit 1511 rotates, the rotation of the first input unit 1511 is output through the output unit 1513; when only the second input unit 1512 rotates, the rotation of the second input unit 1512 is output through the output unit 1513; when the first input unit 1511 and the second input unit 1512 rotate in the same direction, the sum of the rotations of the first input unit 1511 and the second input unit 1512 is output through the output unit 1513; and when the first input unit 1511 and the second input unit 1512 rotate in opposite directions, the difference between the rotations of the first input unit 1511 and the second input unit 1512 is output through the output unit 1513. This may be expressed as the following equation:

(where C denotes a rotation of an output unit, A denotes a rotation of a first input unit, and B denotes a rotation of a second input unit.)

By the first differential gear 151 and the second differential gear 152, even when the yaw operator 112 and the actuation operator 113 rotate freely, the output unit of each differential gear rotates independently of the rotations of the yaw operator 112 and the actuation operator 113. Consequently, the output unit of each differential gear moves as much as the sum of (or the difference between) the rotations of the yaw operator 112 and the actuation operator 113 to extract a desired rotating force.

<First Modification of Differential Gear>

Figure 18:
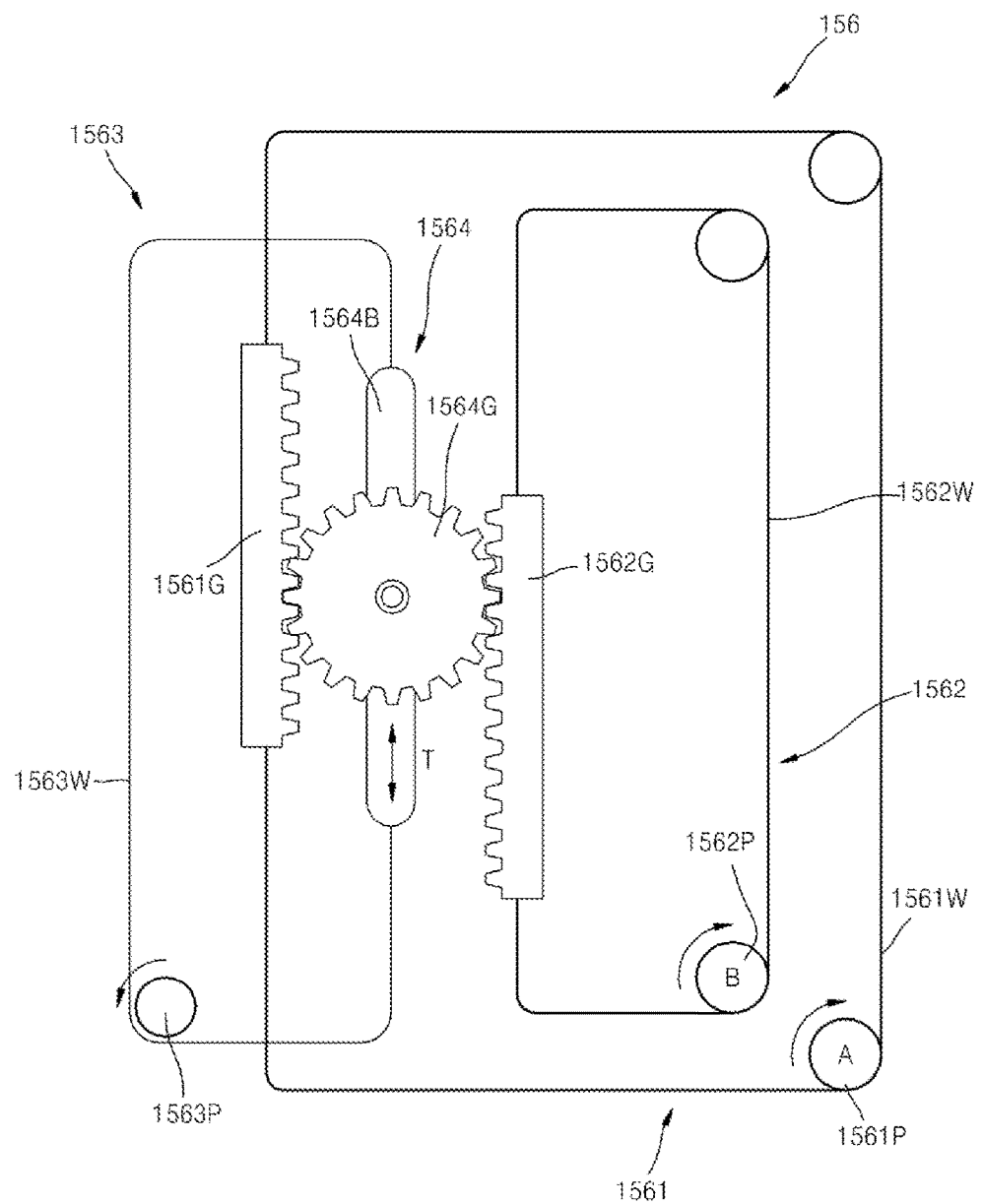
FIG. 18 is a view illustrating a first modification of the differential gear of FIG. 16.

FIG. 18 is a view illustrating a first modification of the differential gear of FIG. 16.

As described above, the differential gear according to the present invention includes two or more input units and one output unit, receives an input of rotating forces from the two or more input units, extracts a desired rotating force from the sum of (or the difference between) the input rotating forces, and outputs the desired rotating force through the output unit.

Referring to FIG. 18, the first modification of the differential gear of the surgical instrument includes a first input unit 1561, a second input unit 1562, an output unit 1563, and a differential control member 1564. The first modification of the differential gear of the surgical instrument illustrated in FIG. 18 may be considered as a structure in which the pulley and wire in the first modification of the differential pulley of the surgical instrument illustrated in FIG. 7 are replaced with a gear.

The first input unit 1561 includes a first pulley 1561P, a first gear 1561G, and a first input wire 1561W. The first pulley 1561P and the first gear 1561G are connected by the first input wire 1561W, so that the first gear 1561G moves vertically when the first pulley 1561P rotates.

The second input unit 1562 includes a second pulley 1562P, a second gear 1562G, and a second input wire 1562W. The second pulley 1562P and the second gear 1562G are connected by the second input wire 1562W, so that the second gear 1562G moves vertically when the second pulley 1562P rotates.

The output unit 1563 includes an output pulley 1563P and an output wire 1563W. The output pulley 1563P and the differential control member 1564 are connected by the output wire 1563W. Thus, when the differential control member 1564 translates, the output pulley 1563P connected with the differential control member 1564 by the output wire 1563W rotates.

The differential control member 1564 includes a differential control gear 1564G and a differential control base 1564B. The differential control gear 1564G is formed to engage with the first gear 1561G and the second gear 1562G. Thus, when the first gear 1561G and the second gear 1562G move vertically, the differential control gear 1564G rotates and translates vertically. That is, the first gear 1561G and the second gear 1562G function as a rack, and the differential control gear 1564G functions as a pinion. Thus, the differential control member 1564 may translate in the direction of an arrow T of FIG. 18. For example, the differential control base 1564B of the differential control member 1564 may be installed on a guide rail (not illustrated), so that the differential control member 1564 may translate along the guide rail in the direction of the arrow T of FIG. 18.

Thus, according to the present invention, when only one of the two or more input units rotates, only the output unit may be rotated without rotating other input units. Also, when the two or more input units rotate together, a single rotating force equal to the sum of (or the difference between) the rotating forces of the two input units may be output through the output unit.

<Second Modification of Differential Gear>

Figure 19:
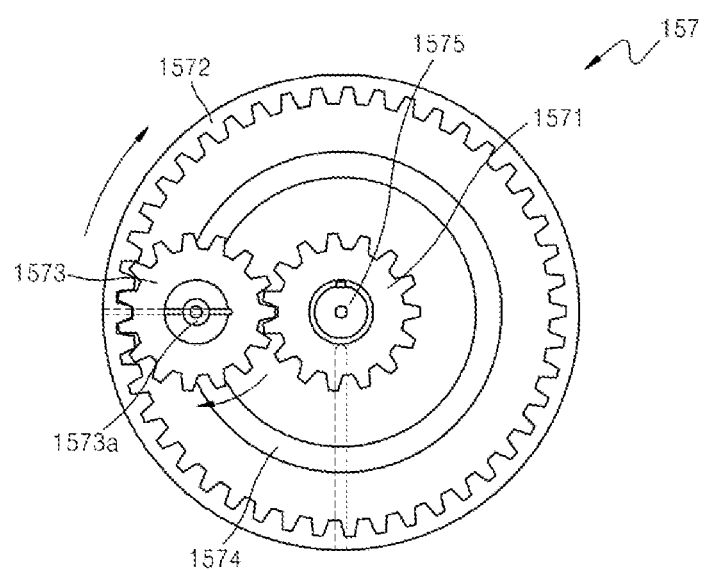
FIG. 19 is a view illustrating a second modification of the differential gear of FIG. 16.

FIG. 19 is a view illustrating a second modification of the differential gear of FIG. 16.

As described above, the differential gear according to the present invention includes two or more input units and one output unit, receives an input of rotating forces from the two or more input units, extracts a desired rotating force from the sum of (or the difference between) the input rotating forces, and outputs the desired rotating force through the output unit.

Referring to FIG. 19, the second modification of the differential gear of the surgical instrument includes a first input unit 1571, a second input unit 1572, an output unit 1574, and a differential control member 1573.

In detail, the first input unit 1571 and the second input unit 1572 may be provided in the form of a gear that may rotate around a central rotating axis 1575. In particular, the second input unit 1572 is provided in the form of a gear that has sawteeth inside a pitch cylinder, and the differential control member 1573 is provided to engage with the gears of the first input unit 1571 and the second input unit 1572. The differential control member 1573 may rotate around a differential control member gear axis 1573a that is connected to the output unit 1574. The output unit 1574 may rotate around the central rotating axis 1575.

When only the first input unit 1571 rotates, the differential control member 1573 engaged with the gear teeth rotates around the differential control member gear axis 1573a and simultaneously rotates around the central rotating axis 1575 of the output unit 1574 connected to the differential control member gear axis 1573a. Also, when only the second input unit 1572 rotates, the differential control member 1573 engaged with the gear teeth rotates around the differential control member gear axis 1573a and simultaneously rotates around the central rotating axis 1575 of the output unit 1574 connected to the differential control member gear axis 1573a. When the first input unit 1571 and the second input unit 1572 rotate in the same direction, the differential control member 1573 and the output unit 1574 rotate around the central rotating axis 1575 in the same direction. In this case, the differential control member 1573 may not rotate around the differential control member gear axis 1573a.

On the other hand, when the first input unit 1571 and the second input unit 1572 rotate in opposite directions, the differential control member 1573 and the output unit 1574 may not rotate around the central rotating axis 1575. In this case, the differential control member 1573 may rotate around the differential control member gear axis 1573a.

Thus, according to the present invention, a single rotating force equal to the sum of (or the difference between) the rotation inputs of two or more input units may be output through the output unit.

While the present invention has been described with reference to exemplary embodiments thereof, it will be understood by those of ordinary skill in the art that various changes in form and details may be made therein without departing from the spirit and scope of the invention as defined by the appended claims. The exemplary embodiments should be considered in descriptive sense only and not for purposes of limitation. Therefore, the scope of the invention is defined not by the detailed description of the invention but by the appended claims, and all differences within the scope will be construed as being included in the present invention.

INDUSTRIAL APPLICABILITY

The differential members according to the embodiments of the present invention may be used in a surgical instrument that may be manually operated to perform laparoscopic operations or various surgical operations.

The invention claimed is:

1. A differential member comprising:
   two or more input units each receiving an input of an amount of rotation motion or translation motion from outside;
   an output unit outputting a single rotation motion or translation motion based on rotation motions or translation motions input to the two or more input units; and
   a differential control member connecting the two or more input units and the output unit;

wherein a rotation motion or translation motion of at least a portion of the differential control member is generated by rotation motions or translation motions input to the two or more input units, and the output unit translates or rotates by a sum of or a difference between the rotation motions or translation motions input to the two or more input units, by the rotation motion or translation motion of at least a portion of the differential control member.

2. A differential member comprising:
two or more input units each receiving an input of an amount of rotation motion or translation motion from outside; and
an output unit outputting a single rotation motion or translation motion based on rotation motions or translation motions input to the two or more input units, wherein the two or more input units rotate or translate independently.

3. A differential member comprising:
two or more input units each receiving an input of an amount of rotation motion or translation motion from outside; and
an output unit outputting a single rotation motion or translation motion based on rotation motions or translation motions input to the two or more input units, wherein when an amount of rotation motion or translation motion is input to only one of the two or more input units, the input rotation motion or translation motion is transmitted only to the output unit.

4. A differential member comprising:
two or more input units each receiving an input of an amount of rotation motion or translation motion from outside; and
an output unit outputting a single rotation motion or translation motion based on rotation motions or translation motions input to the two or more input units, wherein when an amount of rotation motion or translation motion is input to each of the two or more input units, a sum of or a difference between the rotation motions or translation motions input to the two or more input units is output through the output unit.

5. The differential member of claim 4, wherein the rotation motion or translation motion output through the output unit is calculated by a following equation:

$$C=\alpha A \pm \beta B$$

where C denotes an amount of rotation motion or an amount of translation motion output through the output unit, A and B denote an amount of rotation motions or an amount of translation motions input through the two or more input units, and $\alpha$ and $\beta$ denote weights of the input amounts.

6. A differential member comprising:
two or more input units each receiving an input of an amount of rotation motion or translation motion from outside; and
an output unit outputting a single rotation motion or translation motion based on rotation motions or translation motions input to the two or more input units, wherein the rotation motions or translation motions input to the two or more input units do not interfere with each other.

7. A differential member comprising:
two or more input units each receiving an input of an amount of rotation motion or translation motion from outside; and
an output unit outputting a single rotation motion or translation motion based on rotation motions or translation motions input to the two or more input units,
the differential member comprising:
a first input unit comprising two rotating bodies and a first input wire connecting the two rotating bodies and receiving an input of a rotation amount through any one of the two rotating bodies;
a second input unit comprising two rotating bodies and a second input wire connecting the two rotating bodies and receiving an input of a rotation amount through any one of the two rotating bodies;
a differential control member comprising a differential control bar, two rotating bodies respectively formed at both ends of the differential control bar, a differential control wire connecting the two rotating bodies, a first differential joint at which the first input wire and the differential control wire are coupled, and a second differential joint at which the second input wire and the differential control wire are coupled;
an output wire having both ends connected with the differential control member; and
an output unit connected with the output wire and rotated by the output wire when the output wire moves.

8. The differential member of claim 7, wherein
the first input unit comprises a translation motion member connected to the first differential joint to receive an input of a translation motion or comprises two rotating bodies and a first input wire connecting the two rotating bodies to receive an input of a rotation motion, wherein the first input wire and the differential control wire are coupled at the first differential joint to receive an input of a rotation motion amount through any one of the two rotating bodies, and
the second input unit comprises a translation motion member connected to the second differential joint to receive an input of a translation motion or comprises two rotating bodies and a second input wire connecting the two rotating bodies to receive an input of a rotation motion, wherein the second input wire and the differential control wire are coupled at the second differential joint to receive an input of a rotation motion amount through any one of the two rotating bodies.

9. The differential member of claim 7, wherein when the first input unit or the second input unit rotates, the differential control member translates to move the output wire to rotate the output unit.

10. A differential member comprising:
two or more input units each receiving an input of an amount of rotation motion or translation motion from outside; and
an output unit outputting a single rotation motion or translation motion based on rotation motions or translation motions input to the two or more input units,
the differential member comprising:
a first input unit and a second input unit receiving an input of an amount of rotation motion or translation motion;
a first differential control member connected with the first input unit to translate when the first input unit rotates or translates;
a second differential control member connected with the second input unit to translate when the second input unit rotates or translates;
a differential wire wound around rotating bodies provided in the first differential control member and the second differential control member and having a portion at which at least one fixed end is formed; and an output unit connected with at least a portion of the differential wire to rotate when the differential wire moves.

11. The differential member of claim 10, wherein
when the first input unit and the second input unit rotate or translate, the first differential control member and the second differential control member connected therewith translate, and
when the first differential control member and the second differential control member translate, the differential wire connected therewith moves to rotate the output unit.

12. The differential member of claim 10, wherein
the first differential control member comprises a first rotating body, a second rotating body, and a first differential control bar connecting the first rotating body and the second rotating body,
the second differential control member comprises a first rotating body, a second rotating body, and a second differential control bar connecting the first rotating body and the second rotating body, and
the differential wire is wound along the first rotating body of the first differential control member, the second rotating body of the second differential control member, the second rotating body of the first differential control member, and the first rotating body of the second differential control member.

13. The differential member of claim 12, wherein
each of the first rotating body and the second rotating body of the first differential control member is connected with the first input unit such that the first differential control member translates as the first rotating body and the second rotating body of the first differential control member rotate when the first input unit translates or rotates, and
each of the first rotating body and the second rotating body of the second differential control member is connected with the second input unit such that the second differential control member translates as the first rotating body and the second rotating body of the second differential control member rotate when the second input unit translates or rotates.

14. The differential member of claim 10, wherein
the first input unit comprises a translation motion member connected with the first differential control member to receive an input of a translation motion, and
the second input unit comprises a translation motion member connected with the second differential control member to receive an input of a translation motion.

15. The differential member of claim 10, wherein one point of the differential wire and one point of the output unit are fixedly coupled such that the output unit rotates when the differential wire moves.

16. The differential member of claim 10, wherein the fixed end of the differential wire and the output unit are formed on opposite sides with respect to each of the first differential control member and the second differential control member.

17. A differential member comprising:
two or more input units each receiving an input of an amount of rotation motion or translation motion from outside; and
an output unit outputting a single rotation motion or translation motion based on rotation motions or translation motions input to the two or more input units,
the differential member comprising:
a first input unit and a second input unit formed to rotate independently of each other to receive a rotation amount;
an output unit comprising an output rotating body formed to rotate around a rotating axis, an extension portion formed to extend in one direction from the rotating axis of the output rotating body and rotate along with the output rotating body, and a first differential control rotating body and a second differential control rotating body formed at one end portion of the extension portion, formed to rotate around an axis making a predetermined angle with the rotating axis of the output rotating body, and formed to face each other; and
a differential control wire connecting the first input unit, the first differential control rotating body, the second input unit, and the second differential control rotating body.

18. The differential member of claim 17, wherein when rotation amounts are input respectively to the first input unit and the second input unit, the differential control wire is sequentially wound along the first input unit, the first differential control rotating body, the second input unit, and the second differential control rotating body to rotate the output unit by a sum of or a difference between the rotation amounts input respectively to the first input unit and the second input unit.

19. The differential member of claim 17, wherein when a rotation motion amount is input to each of the first input unit and the second input unit, the differential control wire connected thereto moves, the first differential control rotating body or the second differential control rotating body connected to the differential control wire rotates, and the output rotating body connected with the first differential control rotating body and the second differential control rotating body rotates.

20. A differential member comprising:
two or more input units each receiving an input of an amount of rotation motion or translation motion from outside; and
an output unit outputting a single rotation motion or translation motion based on rotation motions or translation motions input to the two or more input units,
the differential member comprising:
a first input unit comprising a first rotating axis and a first input rotating body rotating along with the first rotating axis;
a second input unit comprising a plurality of second input rotating bodies formed to connect with the first input rotating body on one side of the first input unit, formed to face each other, and formed to rotate around a second rotating axis;
a connector comprising a plurality of connecting rotating bodies formed on one side of the second input unit, formed to face each other, and formed to rotate around a fourth rotating axis;
an output unit connecting with the connector and rotating along with a third rotating axis; and
a differential control wire formed to sequentially contact the output unit, one of the two connecting rotating bodies, one of the two second input rotating bodies, the first input rotating body, the other of the two second input rotating bodies, the other of the two connecting rotating bodies, and the output unit and rotate along the output unit, the connector, the second input unit, and the first input unit.

21. The differential member of claim 20, further comprising a coupling member connecting the first input unit and the second input unit,
   wherein the first rotating axis and the second rotating axis are connected to the coupling member, wherein the coupling member and the second rotating axis are fixedly coupled and the coupling member and the first rotating axis are not fixedly coupled.

22. The differential member of claim 20, wherein the first input unit, the second input unit, the connector, and the output unit are sequentially disposed such that the first input unit and the second input unit are formed to rotate together around the second rotating axis.

23. The differential member of claim 20, wherein the first input unit, the connector, the second input unit, and the output unit are sequentially disposed such that the first input unit, the connector, and the second input unit are formed to rotate together around the second rotating axis.

24. A differential member comprising:
   two or more input units each receiving an input of an amount of rotation motion or translation motion from outside; and
   an output unit outputting a single rotation motion or translation motion based on rotation motions or translation motions input to the two or more input units,
   comprising one or more differential gears each comprising:
   two or more input units receiving an input of a rotation amount from the operator from outside; and
   an output unit outputting a single amount of rotation based on the amounts of rotation input to the two or more input units.

25. The differential member of claim 24, wherein the one or more differential gears each comprise:
   a first input unit comprising a first gear;
   a second input unit comprising a second gear facing the first gear; and
   an output unit comprising an output rotating body formed to rotate around a rotating axis, an extension portion formed to extend in one direction from the rotating axis of the output rotating body and rotate along with the output rotating body, and a differential control gear formed to rotate around the extension portion and formed to engage with the first gear and the second gear.

26. The differential member of claim 24, wherein the one or more differential gears each comprise:
   a first input unit comprising a first rotating body and a first gear connected with the first rotating body through a first input wire to translate when the first rotating body rotates;
   a second input unit comprising a second rotating body and a second gear connected with the second rotating body through a second input wire to translate when the second rotating body rotates;
   a differential control member comprising a differential control gear formed to engage with the first gear and the second gear to translate by rotation by the first gear or the second gear when the first gear or the second gear translates; and
   an output unit connected with the differential control member through an output wire to be rotated by the output wire when the differential control member translates.

27. The differential member of claim 24, wherein the one or more differential gears each comprise:
   a first input unit comprising a first gear that translates;
   a second input unit comprising a second gear that translates;
   a differential control member comprising a differential control gear formed to engage with the first gear and the second gear to translate by rotation by the first gear or the second gear when the first gear or the second gear translates; and
   an output unit connected with the differential control member through an output wire to be rotated by the output wire when the differential control member translates.

28. The differential member of claim 26, wherein
   the first gear and the second gear function as a rack, and
   the differential control gear functions as a pinion.

29. The differential member of claim 24, wherein the one or more differential gears each comprise:
   a first input unit provided in the shape of a gear formed to rotate around a predetermined axis;
   a second input unit accommodating the first input unit therein and having sawteeth formed on an inner periphery thereof;
   a differential control member accommodated in the second input unit and interposed between the gear-shaped first input unit and the sawteeth of the second input unit; and
   an output unit formed to rotate around the axis of the first input unit and provide a rotation path such that the differential control member rotates around the axis of the first input unit.

30. The differential member of claim 29, wherein the second input unit and the output unit form an internal gear.

31. The differential member of claim 27, wherein
   the first gear and the second gear function as a rack, and
   the differential control gear functions as a pinion.

* * * * *